(12) United States Patent
Deitz

(10) Patent No.: US 10,959,786 B2
(45) Date of Patent: Mar. 30, 2021

(54) METHODS FOR DATA PROCESSING FOR INTRA-OPERATIVE NAVIGATION SYSTEMS

(71) Applicant: WENZEL SPINE, INC., Austin, TX (US)

(72) Inventor: Adam Deitz, Austin, TX (US)

(73) Assignee: WENZEL SPINE, INC., Austin, TX (US)

( * ) Notice: Subject to any disclaimer, the term of this patent is extended or adjusted under 35 U.S.C. 154(b) by 68 days.

(21) Appl. No.: 16/562,567

(22) Filed: Sep. 6, 2019

(65) Prior Publication Data
US 2020/0085507 A1 Mar. 19, 2020

Related U.S. Application Data

(63) Continuation of application No. 15/169,281, filed on May 31, 2016, now abandoned.

(60) Provisional application No. 62/268,138, filed on Dec. 16, 2015, provisional application No. 62/187,930, filed on Jul. 2, 2015, provisional application No. 62/171,861, filed on Jun. 5, 2015.

(51) Int. Cl.
| | |
|---|---|
| *G06K 9/00* | (2006.01) |
| *A61B 34/20* | (2016.01) |
| *A61B 34/10* | (2016.01) |
| *A61B 5/00* | (2006.01) |

(52) U.S. Cl.
CPC ............ *A61B 34/20* (2016.02); *A61B 5/4566* (2013.01); *A61B 34/10* (2016.02); *A61B 2034/105* (2016.02)

(58) Field of Classification Search
None
See application file for complete search history.

(56) References Cited

U.S. PATENT DOCUMENTS

| | | |
|---|---|---|
| 3,678,190 A | 7/1972 | Cook |
| 4,210,317 A | 7/1980 | Spann et al. |
| 4,404,590 A | 9/1983 | Mayer et al. |
| 4,611,581 A | 9/1986 | Steffee |
| 4,803,734 A | 2/1989 | Onishi et al. |
| 4,805,602 A | 2/1989 | Puno et al. |
| 4,922,909 A | 5/1990 | Little et al. |

(Continued)

FOREIGN PATENT DOCUMENTS

| | | |
|---|---|---|
| AU | 2007238017 B2 | 3/2013 |
| AU | 2016250490 A1 | 11/2016 |

(Continued)

OTHER PUBLICATIONS

Bostman et al., Posterior Spinal Fusion Using Internal Fixation with the Daab Plate, ACTA ortho Scan 55:310-314 (1984).

(Continued)

*Primary Examiner* — Shervin K Nakhjavan
(74) *Attorney, Agent, or Firm* — Buchalter; Cecily Anne O'Regan

(57) ABSTRACT

Disclosed are methods and systems used with surgical navigation systems that enable a user to generate an optimized anatomical dataset for a spine level of interest. The systems and methods allow users to determine a target geometry for a spinal level targeted for spinal surgery. Additionally, the user can project loads across the spinal orthopedic implants and determine a projected subsidence overtime.

14 Claims, 11 Drawing Sheets

(56) References Cited

U.S. PATENT DOCUMENTS

| | | |
|---|---|---|
| 5,000,165 A | 3/1991 | Watanabe |
| 5,019,081 A | 5/1991 | Watanabe |
| 5,058,602 A | 10/1991 | Brody |
| 5,090,042 A | 2/1992 | Bejjani et al. |
| 5,099,859 A | 3/1992 | Bell |
| 5,129,900 A | 7/1992 | Asher et al. |
| 5,203,346 A | 4/1993 | Fuhr et al. |
| 5,316,018 A | 5/1994 | O'Brien |
| 5,320,640 A | 6/1994 | Riddle et al. |
| 5,330,417 A | 7/1994 | Petersen et al. |
| 5,349,956 A | 9/1994 | Bonutti |
| 5,400,800 A | 3/1995 | Jain et al. |
| 5,414,811 A | 5/1995 | Parulski et al. |
| 5,427,116 A | 6/1995 | Noone |
| 5,442,729 A | 8/1995 | Kramer et al. |
| 5,443,505 A | 8/1995 | Wong et al. |
| 5,445,152 A | 8/1995 | Bell et al. |
| 5,474,555 A | 12/1995 | Puno et al. |
| 5,505,208 A | 4/1996 | Toomim et al. |
| 5,548,326 A | 8/1996 | Michael |
| 5,575,792 A | 11/1996 | Errico et al. |
| 5,582,186 A * | 12/1996 | Wiegand ............... G16H 30/40 600/595 |
| 5,582,189 A | 12/1996 | Pannozzo |
| 5,590,271 A | 12/1996 | Klinker |
| 5,640,200 A | 6/1997 | Michael |
| 5,643,263 A | 7/1997 | Simonson |
| 5,683,392 A | 11/1997 | Richelsoph et al. |
| 5,688,274 A | 11/1997 | Errico et al. |
| 5,690,630 A | 11/1997 | Errico et al. |
| 5,707,643 A | 1/1998 | Ogura et al. |
| 5,715,334 A | 2/1998 | Peters |
| 5,725,527 A | 3/1998 | Biedermann et al. |
| 5,740,267 A | 4/1998 | Echerer et al. |
| 5,741,255 A | 4/1998 | Krag et al. |
| 5,748,703 A | 5/1998 | Cosman |
| 5,755,675 A | 5/1998 | Sihvonen |
| 5,772,592 A | 6/1998 | Cheng et al. |
| 5,772,595 A | 6/1998 | Votruba et al. |
| 5,784,431 A | 7/1998 | Kalend et al. |
| 5,792,077 A | 8/1998 | Gomes |
| 5,797,911 A | 8/1998 | Sherman et al. |
| 5,810,006 A | 9/1998 | Votruba et al. |
| 5,813,406 A | 9/1998 | Kramer et al. |
| 5,824,072 A | 10/1998 | Wong |
| 5,838,759 A | 11/1998 | Armistead |
| 5,863,293 A | 1/1999 | Richelsoph |
| 5,879,350 A | 3/1999 | Sherman et al. |
| 5,880,976 A | 3/1999 | DiGioia III et al. |
| 5,885,285 A | 3/1999 | Simonson |
| 5,891,060 A | 4/1999 | McGregor et al. |
| 5,891,145 A | 4/1999 | Morrison et al. |
| 5,899,859 A | 5/1999 | Votruba et al. |
| 5,931,781 A | 8/1999 | De Boer |
| 5,954,674 A | 9/1999 | Fuhr |
| 5,964,760 A | 10/1999 | Richelsoph |
| 6,002,959 A | 12/1999 | Steiger et al. |
| 6,010,503 A | 1/2000 | Richelsoph et al. |
| 6,019,759 A | 2/2000 | Rogozinski |
| 6,022,350 A | 2/2000 | Ganem |
| 6,049,740 A | 4/2000 | Whitehead et al. |
| 6,074,391 A | 6/2000 | Metz-Stavenhagen et al. |
| 6,075,905 A | 6/2000 | Herman et al. |
| 6,077,262 A | 6/2000 | Schlapfer et al. |
| 6,090,111 A | 7/2000 | Nichols |
| 6,132,430 A | 10/2000 | Wagner |
| 6,141,579 A | 10/2000 | Bonutti |
| 6,155,993 A | 12/2000 | Scott |
| 6,248,105 B1 | 6/2001 | Schlapfer et al. |
| 6,269,565 B1 | 8/2001 | Inbar et al. |
| 6,276,799 B1 | 8/2001 | van Saarloos et al. |
| 6,280,395 B1 | 8/2001 | Appel et al. |
| 6,290,703 B1 | 9/2001 | Ganem |
| 6,298,259 B1 | 10/2001 | Kucharczyk et al. |
| 6,351,547 B1 | 2/2002 | Johnson et al. |
| 6,427,022 B1 | 7/2002 | Craine et al. |
| 6,428,490 B1 | 8/2002 | Kramer et al. |
| 6,432,053 B1 | 8/2002 | Fecht et al. |
| 6,434,264 B1 | 8/2002 | Asar |
| 6,451,021 B1 | 9/2002 | Ralph et al. |
| 6,469,717 B1 | 10/2002 | Wineke et al. |
| 6,471,705 B1 | 10/2002 | Biedermann et al. |
| 6,497,672 B2 | 12/2002 | Kramer |
| 6,524,315 B1 | 2/2003 | Selvitelli et al. |
| 6,540,749 B2 | 4/2003 | Schafer et al. |
| 6,544,186 B2 | 4/2003 | Shelby et al. |
| 6,547,790 B2 | 4/2003 | Harkey et al. |
| 6,560,476 B1 | 5/2003 | Pelletier et al. |
| 6,565,565 B1 | 5/2003 | Yuan et al. |
| 6,608,916 B1 | 8/2003 | Wei et al. |
| 6,608,917 B1 | 8/2003 | Wei et al. |
| 6,697,659 B1 | 2/2004 | Bonutti |
| 6,698,885 B2 | 3/2004 | Berger et al. |
| 6,719,750 B2 | 4/2004 | Varner et al. |
| 6,726,691 B2 | 4/2004 | Osorio et al. |
| 6,755,839 B2 | 6/2004 | Van Hoeck et al. |
| 6,866,643 B2 | 3/2005 | Kramer |
| 6,882,744 B2 | 4/2005 | Oosawa |
| 6,890,312 B1 | 5/2005 | Priester et al. |
| 6,907,280 B2 | 6/2005 | Becerra et al. |
| 6,963,768 B2 | 11/2005 | Ho et al. |
| 6,964,781 B2 | 11/2005 | Brubaker |
| 6,990,368 B2 | 1/2006 | Simon et al. |
| 7,000,271 B2 | 2/2006 | Varadharajulu |
| 7,034,063 B2 | 4/2006 | Nienhaus et al. |
| 7,046,830 B2 | 5/2006 | Gerard et al. |
| 7,050,537 B2 | 5/2006 | Tsujii |
| 7,110,587 B1 | 9/2006 | Natanzon et al. |
| 7,117,027 B2 | 10/2006 | Zheng et al. |
| 7,127,090 B2 | 10/2006 | Kreang-Arekul et al. |
| 7,133,066 B2 | 11/2006 | Bourret |
| 7,153,307 B2 | 12/2006 | Scribner et al. |
| 7,158,661 B2 | 1/2007 | Inoue |
| 7,184,814 B2 | 2/2007 | Lang et al. |
| 7,194,120 B2 | 3/2007 | Wicker et al. |
| 7,235,076 B2 | 6/2007 | Pacheco |
| 7,241,303 B2 | 7/2007 | Reiss et al. |
| 7,243,387 B2 | 7/2007 | Schindler |
| 7,266,406 B2 | 9/2007 | Kroeckel |
| 7,300,441 B2 | 11/2007 | Haid et al. |
| 7,333,649 B2 | 2/2008 | Nagata et al. |
| 7,338,526 B2 | 3/2008 | Steinberg |
| 7,502,641 B2 | 3/2009 | Breen |
| 7,567,834 B2 * | 7/2009 | Clayton ................... A61B 5/06 600/424 |
| 7,679,971 B1 | 3/2010 | Yu |
| 7,697,971 B1 | 4/2010 | Green et al. |
| 7,747,309 B2 | 6/2010 | Prince |
| 7,780,703 B2 | 8/2010 | Yuan et al. |
| 7,799,077 B2 | 9/2010 | Lang et al. |
| 7,835,778 B2 | 11/2010 | Foley et al. |
| 7,837,635 B2 | 11/2010 | Lissek et al. |
| 7,881,767 B2 | 2/2011 | Strommer et al. |
| 7,935,133 B2 | 5/2011 | Malek |
| 7,955,133 B2 | 6/2011 | Scheele et al. |
| 7,974,677 B2 | 7/2011 | Mire et al. |
| 8,043,337 B2 | 10/2011 | Klyce et al. |
| 8,048,120 B1 | 11/2011 | Fallin et al. |
| 8,070,817 B2 | 12/2011 | Gradl et al. |
| 8,114,132 B2 | 2/2012 | Lyons et al. |
| 8,128,659 B2 | 3/2012 | Ginsberg et al. |
| 8,157,842 B2 | 4/2012 | Phan et al. |
| 8,394,144 B2 | 3/2013 | Zehavi et al. |
| 8,660,329 B2 * | 2/2014 | Skalli ..................... G06T 7/55 382/131 |
| 8,676,293 B2 | 3/2014 | Breen et al. |
| 8,777,878 B2 | 7/2014 | Deitz |
| 8,876,830 B2 | 11/2014 | Hodorek et al. |
| 8,906,027 B2 | 12/2014 | Roche |
| 9,023,050 B2 | 5/2015 | Lang et al. |
| 9,491,415 B2 * | 11/2016 | Deitz ................... A61B 5/7278 |
| 9,795,451 B2 * | 10/2017 | Gorek ................... A61B 6/461 |
| 2002/0077543 A1 * | 6/2002 | Grzeszczuk .......... H04N 13/221 600/424 |

(56) References Cited

U.S. PATENT DOCUMENTS

| | | |
|---|---|---|
| 2002/0120272 A1 | 8/2002 | Yuan et al. |
| 2003/0073901 A1 | 4/2003 | Simon et al. |
| 2003/0081837 A1 | 5/2003 | Williame et al. |
| 2003/0086596 A1 | 5/2003 | Hipp et al. |
| 2003/0220648 A1 | 11/2003 | Osorio et al. |
| 2003/0225327 A1 | 12/2003 | Willen et al. |
| 2004/0010260 A1 | 1/2004 | Scribner et al. |
| 2004/0098803 A1 | 5/2004 | Schindler |
| 2004/0141591 A1 | 7/2004 | Izuhara |
| 2004/0172145 A1 | 9/2004 | Varadharajulu |
| 2004/0225296 A1 | 11/2004 | Reiss et al. |
| 2005/0034684 A1 | 2/2005 | Lopez et al. |
| 2005/0107681 A1 | 5/2005 | Griffiths |
| 2005/0148948 A1 | 7/2005 | Caputa |
| 2005/0149050 A1* | 7/2005 | Stifter ............ A61B 34/20 606/102 |
| 2005/0187459 A1 | 8/2005 | Trequattrini et al. |
| 2005/0222505 A1 | 10/2005 | Damadian et al. |
| 2005/0240193 A1 | 10/2005 | Layne et al. |
| 2005/0245817 A1* | 11/2005 | Clayton ............ A61B 5/06 600/424 |
| 2005/0259794 A1 | 11/2005 | Breen |
| 2006/0020196 A1 | 1/2006 | Elias |
| 2006/0120583 A1* | 6/2006 | Dewaele ............ G06T 3/0068 382/128 |
| 2006/0149136 A1 | 7/2006 | Seto et al. |
| 2006/0185091 A1 | 8/2006 | Jackson |
| 2006/0264952 A1 | 11/2006 | Nelson et al. |
| 2007/0030346 A1 | 2/2007 | Feuerlein |
| 2007/0067034 A1 | 3/2007 | Chirico et al. |
| 2007/0129634 A1 | 6/2007 | Hickey et al. |
| 2007/0219445 A1* | 9/2007 | Liebschner ............ A61B 6/12 600/431 |
| 2007/0276501 A1* | 11/2007 | Betz ............ A61F 2/30942 623/17.16 |
| 2007/0287900 A1* | 12/2007 | Breen ............ A61B 5/0488 600/407 |
| 2008/0009773 A1 | 1/2008 | Harrison et al. |
| 2008/0039867 A1 | 2/2008 | Feussner et al. |
| 2008/0103601 A1 | 5/2008 | Biro et al. |
| 2008/0114267 A1* | 5/2008 | Lloyd ............ A61B 34/20 600/587 |
| 2008/0125678 A1 | 5/2008 | Breen |
| 2008/0147188 A1 | 6/2008 | Steinberg |
| 2008/0161680 A1 | 7/2008 | von Jako et al. |
| 2009/0024164 A1* | 1/2009 | Neubardt ............ A61B 5/1077 606/242 |
| 2009/0089034 A1 | 4/2009 | Penney et al. |
| 2009/0099481 A1 | 4/2009 | Deitz |
| 2009/0253095 A1 | 10/2009 | Salcedo et al. |
| 2009/0285466 A1 | 11/2009 | Hipp et al. |
| 2009/0297012 A1* | 12/2009 | Brett ............ G06K 9/6263 382/132 |
| 2010/0030232 A1* | 2/2010 | Zehavi ............ A61F 2/4611 606/130 |
| 2010/0086185 A1* | 4/2010 | Weiss ............ A61B 5/0042 382/131 |
| 2010/0174673 A1 | 7/2010 | Skalli et al. |
| 2010/0191088 A1 | 7/2010 | Anderson et al. |
| 2010/0249534 A1 | 9/2010 | Pierce et al. |
| 2011/0029020 A1 | 2/2011 | Gordon et al. |
| 2011/0054531 A1 | 3/2011 | Lamborne et al. |
| 2011/0054851 A1 | 3/2011 | Heller et al. |
| 2011/0066186 A1 | 3/2011 | Boyer et al. |
| 2011/0092859 A1* | 4/2011 | Neubardt ............ A61B 90/06 600/594 |
| 2011/0144692 A1 | 6/2011 | Saladin et al. |
| 2011/0166600 A1 | 7/2011 | Lamborne et al. |
| 2011/0224731 A1 | 9/2011 | Smisson, III et al. |
| 2011/0224740 A1 | 9/2011 | Smisson, III et al. |
| 2011/0313458 A1 | 12/2011 | Butler et al. |
| 2011/0319936 A1 | 12/2011 | Gordon et al. |
| 2012/0010662 A1 | 1/2012 | O'Neil et al. |
| 2012/0016418 A1 | 1/2012 | Chin et al. |
| 2012/0078304 A1 | 3/2012 | Jensen et al. |
| 2012/0078305 A1 | 3/2012 | Wang et al. |
| 2012/0083844 A1 | 4/2012 | Linares |
| 2012/0083846 A1 | 4/2012 | Wallenstein et al. |
| 2012/0089184 A1 | 4/2012 | Yeh |
| 2012/0095512 A1 | 4/2012 | Nihalani |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0109205 A1 | 5/2012 | Mitchell et al. |
| 2012/0123475 A1 | 5/2012 | Ahn et al. |
| 2012/0136390 A1 | 5/2012 | Butler et al. |
| 2012/0143090 A1* | 6/2012 | Hay ............ G06T 7/0014 600/587 |
| 2012/0143252 A1 | 6/2012 | Robinson |
| 2012/0150228 A1 | 6/2012 | Zappacosta et al. |
| 2012/0158061 A1 | 6/2012 | Koch et al. |
| 2012/0158063 A1 | 6/2012 | Altarac et al. |
| 2012/0172700 A1* | 7/2012 | Krishnan ............ G16H 30/20 600/407 |
| 2012/0310292 A1 | 12/2012 | Smisson, III et al. |
| 2012/0321168 A1 | 12/2012 | Deitz |
| 2013/0060146 A1* | 3/2013 | Yang ............ A61B 6/032 600/476 |
| 2013/0131486 A1* | 5/2013 | Copf ............ A61F 2/30942 600/407 |
| 2013/0203031 A1 | 8/2013 | McKinnon et al. |
| 2014/0003684 A1* | 1/2014 | Ayed ............ G06T 7/136 382/128 |
| 2014/0108983 A1* | 4/2014 | Dobkin ............ G06F 3/0484 715/771 |
| 2014/0296654 A1 | 10/2014 | Breen et al. |
| 2014/0323845 A1* | 10/2014 | Forsberg ............ A61B 5/4561 600/407 |
| 2015/0320341 A1 | 11/2015 | Breen et al. |
| 2016/0028998 A1 | 1/2016 | Deitz et al. |
| 2016/0354161 A1 | 12/2016 | Deitz |
| 2018/0061048 A1* | 3/2018 | Weiss ............ G06T 7/0012 |
| 2018/0122075 A1 | 5/2018 | Deitz et al. |
| 2019/0156482 A1 | 5/2019 | Deitz et al. |

FOREIGN PATENT DOCUMENTS

| | | |
|---|---|---|
| CA | 2821110 A1 | 6/2012 |
| DE | 20009875 U1 | 9/2000 |
| EP | 0260044 A1 | 3/1988 |
| EP | 0176728 B1 | 7/1989 |
| EP | 0804032 A2 | 10/1997 |
| EP | 1123686 A2 | 8/2001 |
| EP | 1219240 A2 | 7/2002 |
| EP | 1123686 A3 | 8/2002 |
| EP | 1519681 B1 | 11/2006 |
| JP | 07284020 A2 | 10/1995 |
| WO | 9810722 A1 | 3/1998 |
| WO | 0012033 A1 | 3/2000 |
| WO | 2001093764 A1 | 12/2001 |
| WO | 2004004570 A1 | 1/2004 |
| WO | 2005007217 A2 | 1/2005 |
| WO | 2006027734 A1 | 3/2006 |
| WO | 2007121337 A2 | 10/2007 |
| WO | 2009049062 A2 | 4/2009 |
| WO | 2011038236 A2 | 3/2011 |
| WO | 2012082615 A2 | 6/2012 |
| WO | 2013158960 A1 | 10/2013 |
| WO | 2015040552 A1 | 3/2015 |
| WO | 2015054543 A1 | 4/2015 |

OTHER PUBLICATIONS

Globus Medical SP-Fix Spinous Process Fixation Plate: Surgical Technique, pp. 1-12 (2011).

Oregon Health & Science University, OHSU Surgeons Find New Way to Fix Painful Broken Ribs, http://www.ohsu.edu/ohsuedu/newspub/releases/062706rubs.cfm (Jun. 27, 2006).

Saint John's Health Center, Saint John's Spine Surgeon Uses ILIF Procedure to Treat Lumbar Spinal Stenosis (2009).

(56) References Cited

OTHER PUBLICATIONS

Senegas, Minimally Invasive Dynamic Stabilization of the Lumbar Motion Segment with an Interspinous Implant, Minimally Invasive Spine Surgery pp. 459-465 (2006).
Biomedical Business & Technology, "Minimally invasive procedures are the name of the game", Jun. 5, 2008. http://search.proquest.com/professional/docview/1083067354?accountid=157282.
Breen, et al. Lumbar spine motion palpation compared with objective intervertebral motion analysis: preliminary findings. Euro. J. Chiro. 50: 27-32 (2002).
Breen, et al. Quantitative analysis of lumbar spine intersegmental motion. European Journal of Physical Medicine and Rehabilitation 3(5): 182-90 (1993).
Breen, et al. Spine kinematics: a digital videofluoroscopic technique, J. Biomed. Engr. 11: 224-8 (1989).
Bryant. Method for determining vertebral body positions in the sagittal plane using skin markers. Spine 14(3): 258-65 (1989).
Carragee, et al. Low-pressure positive Discography in subjects asymptomatic of significant low back pain illness. Spine. 31(5): 505-509 (2006).
Cholewicki, et al. Method for measuring vertebral kinematics from videofluoroscopy. Clinical Biomechanics 6: 73-8 (1991).
Cholewicki, et al. Lumbar posterior ligament involvement during extremely heavy lifts estimated from fluoroscopic measurements. J. Biomechanics 25(1): 17-28 (1992).
Esses, et al. Kinematic evaluation of lumbar fusion techniques. Spine 21(6): 676-84 (1996).
Fujiwara, et al. The relationship between disc degeneration, facet joint osteoarthritis, and stability of the degenerative lumbar spine. J. Spinal Disorders 13: 444-50 (2000).
Harada, et al. Cineradiographic motion analysis of normal lumbar spine during forward and backward flexion. Spine 25: 1932-7 (2000).
Johnsson, et al. Mobility of the lower lumbar spine after posterolateral fusion determined by roentgen stereophotogrammetric analysis. Spine 15: 347-50 (1990).
Jones, Cervical spine cineradiography after traffic accidents. Archives of Surgery 85: 974-81 (1962).
Kaigle, et al. Muscular and kinematic behavior of the lumbar spine during flexion-extension. Journal of Spinal Disorders. 11(2): 163-174 (1998).
Kleissen, et al., "Simultaneous Measurement of Surface EMG and Movements for Clinical USE" Med. Biol. Eng. Comp. 27(3): 291-97 (1989).
Kondracki, Digital Videofluoroscopy, Manual Therapy 1, 146-48 (1996).
Lariviere, et al. A triaxial dynamometer to monitor lateral bending and axial rotation moments during static trunk extension efforts. Clin Biomech 16(1):80-3 (2001).
Lawrence, Disc degeneration. Its frequency and relationship to symptoms. Annals of Rheumatic Diseases 28:121-38 (1969).
Lee et al. Development and validation of a new technique for assessing lumbar spine motion, Spine 27(8): E215-20 (2002).
McGregor et al. Spinal motion in lumbar degenerative disc disease. J. Joint Surg (Br). 80-B: 1009-1013 (1998).
Medical Device & Surgery Technology Week, "Medical Devices; Release of surgical navigation software for knee implant system announced", Mar. 27, 2005:238, ISSN: 15371409. http://search.proquest.com/professional/docview/206901375?accountid=157282.
Medical Devices & Surgical Technology Week, "Orthopedics; Computer aided 'tools' to usher in next surgical revolution", Mar. 17, 2002; ISSN: 15371409. http://search.proquest.com/professional/docview206902428?accountid=17282.
Quick, et al. Real-Time MRI of Joint Movement with True FISP, J. Mag. Res. Imaging 15(6):710-15 (2002).
Schlenzka, D. et al., "Computer-assisted spine surgery", Eur Spine J (2000) 9 (Suppl 1):S57-S64.
Stokes, et al. Trunk muscular activation patterns and responses to transient force perturbation in persons with self-reported low back pain. Eur Spine J. 15:658-667 (2006).
Takayanagi, et al. Using cineradiography for continuous dynamic-motion analysis of the lumbar spine. Spine 26(17): 1858-1865 (2001).
Teyhen, et al., A New Technique for Digital Fluoriscopic Video Assessment of Sagittal Plane Lumbar Spine Motion, Spine vol. 30(14), pp. E406-E413 (2005).
Waddell, G. The Back Pain Revolution. Churchill Livingstone. Edinburgh. 1998; Ch2 p. 23.
Wong, et al. Continuous dynamic spinal motion analysis. Spine. 2006; 31(4): 414-419.
Zheng, et al. Automatic Lumbar Vertebrae Segmentation in Fluoroscopic Images via Optimised Concurrent Hough Transform, 23rd Annual International Conf of IEEE Engineering in Med and Biology (2001).
Zheng, et al. Lumbar spine visualisation based on kinematic analysis from videofluoroscopic imaging. Medical Engineering and Physics. 2003; 25: 171-179.

\* cited by examiner

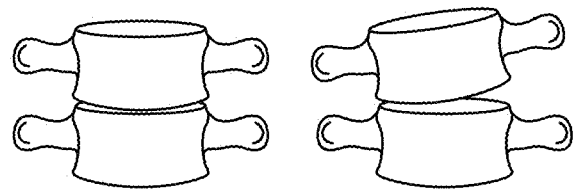
CURRENT   TARGET: ADH, PDH, OFFSET
FIG. 1
FIG. 2A
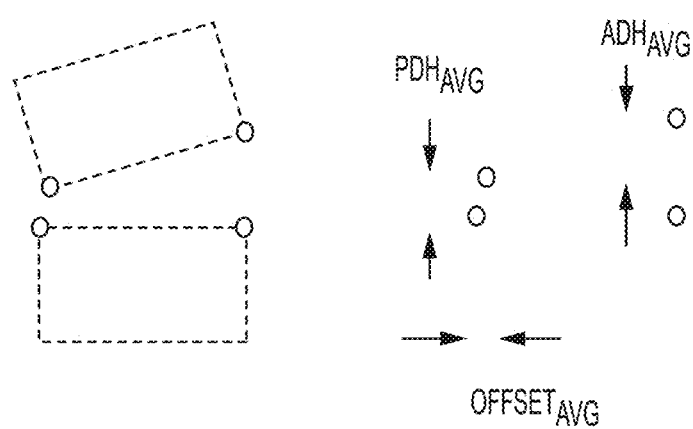
FIG. 2B
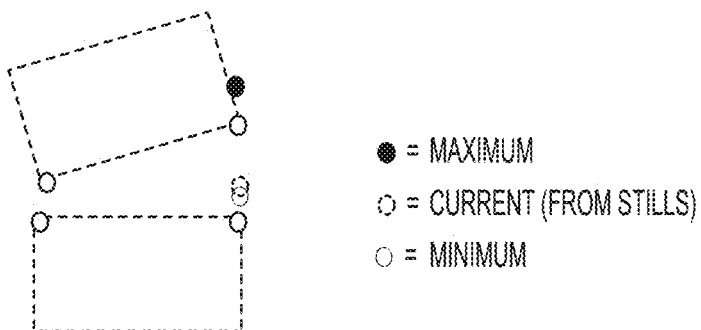
● = MAXIMUM
◐ = CURRENT (FROM STILLS)
○ = MINIMUM
FIG. 2C
FIG. 2D

TARGET SURGICAL CONSTRUCT

∠(L4/L5)SAG = 22°

160%
50%
3.1 mm
105%
1.7 mm
55%
0%
+0.9 mm
0.5 mm
ANTERIOR

| APPLY SUBSIDENCE ASSUMPTIONS? | ○ NO  ⊙ YES | |
|---|---|---|
| ANTERIOR SUBSIDENCE (%AHD) | | POSTERIOR SUBSIDENCE (%PDH) |
| L4 ▷ 10% | | ▷ 10% |
| L5 ▷ 10% | | ▷ 10% |
| TOTAL 20% (0.4 mm) | | 20% (0.7 mm) |

IMPLANT DIMENSIONS:

∠ = 22°
∠ P-LL = 8°
HANT = 3.9 mm
HPOST = 1.9 mm
DSUP = 26 mm
DINF = 25 mm

[RESTORE DEFAULTS]

GRAVITATIONAL FORCES:

SHEER = 17 N (40%)
COMPRESSIVE = 8 N/M² (115%)
(% OF USER DEFINED MAXIMUM)

| ACTUAL VS. TARGET | REQUIRED TO ACHIEVE TARGET CONSTRUCT | | | DISPLAY SETTINGS |
|---|---|---|---|---|
| ○ SHOW ACTUAL VALUES | OFFSET | PDH | ADH | ☐ SHOW mm |
| ⊙ SHOW TARGET CONSTRUCT | ⇓ | ⇑ | ⇑ | ☑ SHOW ANGLES |
| 👆 SHOW CURRENT  [CAPTURE] | 0.3 mm | 1.0 mm | 2.3 mm | ☑ SHOW % MAX MOBILITY |
| | | | | ☑ SET A/P HORIZON TO TOP OF L5 |

EDIT / CONFIRM ADDITIONAL LORDOSIS TO CORRECT SAGITTAL ALIGNMENT

| PRE-OP | CHANGE VS PRE-OP: SEGMENTAL LORDOSIS (SUMMED ACROSS ALL FUSION LEVELS) | L1-S1 SAGITTAL ALIGNMENT CORRECTION | CORRECTION FOR ANTICIPATED SUBSIDENCE * (SUMMED ACROSS ALL FUSION LEVELS) | POST-OP |
|---|---|---|---|---|
| PI-LL=X° △ SA | +X° | +X° [+][−] OK | +X° | PI-LL=X° △ SA |
| | COMPUTED VALUE BASED ON DEFAULT SETTINGS | | | |

FIG. 8

ENTER ANY DESIRED CORRECTIONS TO UPPER / LOWER LUMBAR ARCS

| | PRE-OP | CHANGE VS PRE-OP: SEGMENTAL LORDOSIS (SUMMED ACROSS ALL FUSION LEVELS) | L1-S1 SAGITTAL ALIGNMENT CORRECTION | CORRECTION FOR ANTICIPATED SUBSIDENCE * (SUMMED ACROSS ALL FUSION LEVELS) | POST-OP |
|---|---|---|---|---|---|
| APEX OF LUMBAR CURVE △ L1 LX UPPER ARC | XX° | +X° | +X° [+] | +X° | XX° |
| S1 LOWER ARC | XX° | +X° | +X° [+] | +X° | XX° |
| LORDOSIS TYPE | X △ SA | | | | X △ SA |
| PELVIC TILT | X° | | | | X° |

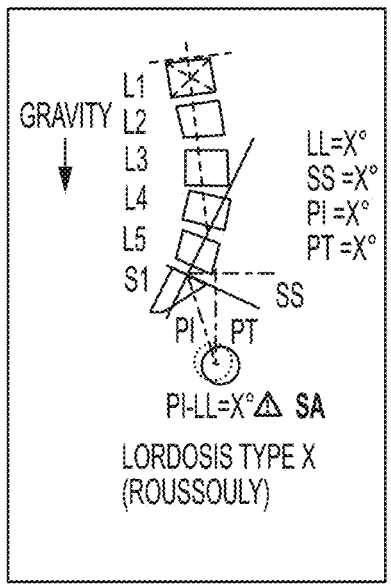
FIG. 9A
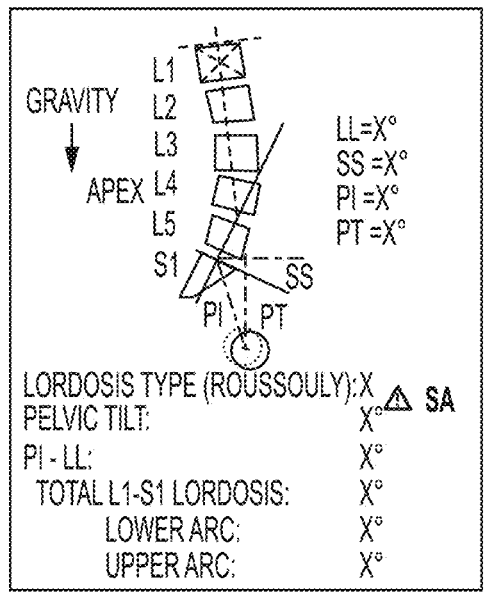
FIG. 9B
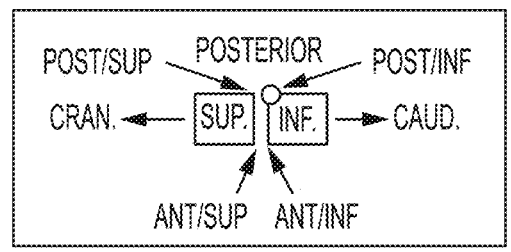
FIG. 10
|  | L1/L2 | L2/L3 | L3/L4 | L4/L5 | L5/S1 |
|---|---|---|---|---|---|
| PANJABI, ET. AL. (1992) | 24% | 20% | 16% | 26% | 14% |
| STAGNARA, ET. AL. (1988) | 14% | 23% | 18% | 18% | 27% |
| AVERAGE | 18% | 18% | 18% | 21% | 25% |
FIG. 11

W(LEVEL) = [PT WT] × P(LEVEL)

P(LEVEL) = PROPORTION OF TOTAL WEIGHT ABOVE THE SUPERIOR VERTEBRAL BODY OF THAT LEVEL.

- USE DEMPSTERS BODY SEGMENT DATA TO GROSS ESTIMATE (WHICH INCLUDES THE FULL LUMBAR OR CERVICAL REGION)

| LUMBAR | CERVICAL |
  |---|---|
  | UPPER EXTREMITY × 2 | HEAD |
  | HEAD | |
  | SHOUDER | |
  | THORAX | |
  | ABDOMEN | |

- BREAKDOWN ABDOMEN AND HEAD BASED ON DATA COLLECTED FROM VMA IMAGES

W(LEVEL) = [PT WT] × P(LEVEL)

P(LEVEL) = PROPORTION OF TOTAL WEIGHT ABOVE THE SUPERIOR VERTEBRAL BODY OF THAT LEVEL.

- USE DEMPSTERS BODY SEGMENT DATA TO GROSS ESTIMATE (WHICH INCLUDES THE FULL LUMBAR OR CERVICAL REGION)

LUMBAR  
  UPPER EXTREMITY × 2  
  HEAD  
  SHOULDER  
  THORAX  
  ABDOMEN

CERVICAL  
  HEAD

- BREAKDOWN ABDOMEN AND HEAD BASED ON DATA COLLECTED FROM VMA IMAGES

METHODS FOR DATA PROCESSING FOR INTRA-OPERATIVE NAVIGATION SYSTEMS

CROSS-REFERENCE

This application is a continuation application of U.S. patent application Ser. No. 15/169,281 filed May 31, 2016, which claims the benefit of U.S. Provisional Application No. 62/171,861 filed Jun. 5, 2015, entitled Methods for Determining the Target Geometry for a Level Targeted for Spinal Surgery, for Determining the Safe Operating Range of Spinal Joints During Surgery, and for Modeling and Projecting Various Loads Across Spinal Orthopedic Implants, and U.S. Provisional Application No. 62/187,930 filed Jul. 2, 2015, entitled Methods for Determining the Target Geometry for a Level Targeted for Spinal Surgery, for Determining the Safe Operating Range of Spinal Joints During Surgery, and for Modeling and Projecting Various Loads Across Spinal Orthopedic Implants, and U.S. Provisional Application No. 62/268,138 filed Dec. 16, 2015, entitled Methods and Systems for Managing Spinal Surgery in an Operating Environment, which applications are incorporated herein by reference.

BACKGROUND OF THE INVENTION

One of the most prevalent joint problems is back pain, particularly in the "small of the back" or lumbosacral (L4-S1) region. In many cases, the pain severely limits a person's functional ability and quality of life. Such pain can result from a variety of spinal pathologies. Through disease or injury, the vertebral bodies, intervertebral discs, laminae, spinous process, articular processes, or facets of one or more spinal vertebrae can become damaged, such that the vertebrae no longer articulate or properly align with each other. This can result in an undesired anatomy, loss of mobility, and pain or discomfort. Duke University Medical Center researchers found that patients suffering from back pain in the United States consume more than $90 billion annually in health care expenses, with approximately $26 billion being directly attributable to treatment. Additionally, there is a substantial impact on the productivity of workers as a result of lost work days. Similar trends have also been observed in the United Kingdom and other countries.

As part of the diagnostic process of determining the cause of pain coming from a joint such as the lumbar spine, health care providers rely on an understanding of joint anatomy and mechanics when evaluating a subject's suspected joint problem and/or biomechanical performance issue. Currently available orthopedic diagnostic methods are capable of detecting a limited number of specific and treatable defects. These techniques include X-Rays, MRI, discography, and physical exams of the patient. In addition, spinal kinematic studies such as flexion/extension X-rays are used to specifically detect whether or not a joint has dysfunctional motion. These methods have become widely available and broadly adopted into the practice of treating joint problems and addressing joint performance issues.

What us needed are new devices and methods for determining the target geometry for a level targeted for spinal surgery. Additionally, devices and methods for the safe operating range of spinal joints during surgery. Still other needs include devices and methods for modeling and projecting various loads across spinal orthopedic implants.

SUMMARY OF THE INVENTION

Disclosed are devices and methods for determining the target geometry for a level targeted for spinal surgery. Additionally, disclosed are devices and methods for the safe operating range of spinal joints during surgery. Also included are devices and methods for modeling and projecting various loads across spinal orthopedic implants.

An aspect of the disclosure is directed to a machine readable medium containing instructions stored on a non-transitory computer readable medium that, when executed by a computing device, cause the computing device to perform a method, the method comprising: receiving an input dataset comprising one or more medical images containing a spine level of interest for a patient; and generating an optimized anatomical dataset for the spine level of interest wherein the optimized anatomical data set comprises one or more of a target disc height, a target anterior-posterior offset, and a target lordosis angle, and further wherein the step of generating an optimized anatomical dataset for the spine level of interest comprises the steps of: identifying zero, one or more visible spine levels in the one or more medical images to exclude from analysis; and accessing one or more image-derived measurements of a disc height measurement, an anterior-posterior offset measurement, and a sagittal lordosis angle measurement for one or more non-excluded spine levels; and applying a function to the one or more measurements from accessing one or more image-derived measurements to generate an optimized value for the spine level of interest for one or more of the target disc height, the target anterior-posterior offset, and the target lordosis angle. The optimized anatomical data set can comprises two or more of a target disc height, a target anterior-posterior offset, and a target lordosis angle. Additionally, the function can receive an input and applies one or more adjustments to correct for an assumed post-operative subsidence of an interbody device over time. In at least some configurations, the one or more adjustments is a disc height adjustment, an anterior-posterior offset adjustment, and a lordosis angle adjustment. The one or more medical images excluded from analysis can be excluded independently for one or more of an excluded disc height measurement, an excluded anterior-posterior offset, and an excluded sagittal lordosis angle. The function can also be one of an average function and a distribution function, and further wherein an input is selected from a medical literature. A surgical navigation system user may also specify a gross lordosis target for an entire region of a spine and wherein the function distributes one or more gross lordosis regional targets across a user-specified set of levels targeted for fusion surgery.

Another aspect of the disclosure is directed to a processor for generating estimates of a weight carried at a spine level of interest, wherein the processor is programmed to execute: accessing an input dataset for a patient comprising a weight of the patient, one or more image-derived measurements of a spatial relationships between two or more vertebral bodies visible within one or more images; allowing a user to specify a spine level of interest; and projecting an estimated weight carried at the spine level of interest by: looking-up one or more values from a previously published mass distribution function, wherein the mass distribution function comprises a set of percentage values associated with various bodily regions such that the sum of the set of percentage values equals 100%; summing x from the mass distribution function elements for all bodily regions cranial to a spinal region of interest; calculating y from the image-derived measurements of the spatial relationships between vertebral bodies from the input dataset, by determining an estimated percentage of the region of interest that is cranial to a spinal level of interest; summing x and y; and multiplying the sum of x and y by a weight of the patient to determine the weight carried at the spine level of interest. Additionally, the processor is configurable to calculate a sheer and a compressive component of the weight carried at the spine level of interest, using the image-derived measurements of the angulation between vertebral body endplates and a plumb line. In at least some configurations, the input dataset contains patient-specific data and wherein the computational routine incorporates a lookup function that returns a mass distribution which is a function of the patient-specific data. The patient-specific data can be selected from, for example, age, gender, and height. Additionally, the previously published mass distribution function is one selected by the user from among a set of available functions.

Still another aspect of the disclosure is directed to a processor for use with surgical navigation systems used for spinal surgery wherein the processor is programmed to execute: receiving an input dataset comprising one or more medical images containing a spine level of interest; and generating measurements of an operating range of the spine level of interest, comprising measurements of at least one of a minimum linear displacement between a pair of adjacent vertebral body corner-points from the spine level of interest and a maximum linear displacement between a pair of adjacent vertebral body corner-points from the spine level of interest by executing a computational process comprising: accessing one or more medical images containing the spine level of interest from the input dataset, and further accessing one or more measurements from each image of at least one of the minimum linear displacement and the maximum linear displacement; and applying at least one of a maximum function and a minimum function to the measurement sets to determine a maximum linear displacement value for a pair of adjacent corner points and a minimum linear displacement values for the pair of adjacent corner-points; and rendering data usable by a surgical navigation system based on the operating range measurements. The rendering of data usable by a surgical navigation system can support a visual display of the operating range measurements by the surgical navigation system. Additionally, the data rendered can trigger an alert to a surgical navigation system user when the operating range measurement for the spine level of interest is outside of a user-determined threshold value.

Yet another aspect of the disclosure is directed to a processor for use with a surgical navigation system used for spinal surgery that wherein the processor is programmed to execute: receiving an input dataset comprising one or more medical images, wherein each medical image includes an image of a spinal level of interest, one or more image-derived measurements for each medical image wherein the one or more image-derived measurements are selected from an alignment measurement, a lordosis measurement, a translation measurement, an angulation measurement, and a disc height measurement; allowing a user to specify a data presentation by selecting one or more of the image-derived measurements and by further selecting at least one of a minimum value and a maximum value; identifying a specific image view corresponding to the data presentation wherein an output of an identification process is a reference to an image that corresponds to the user specified data presentation; and generating comparative data between a current status of the patient wherein the generated comparative data uses a measurement from one or more image captured intra-operatively via the surgical navigation system and the data presentation. The measurement of interest can include measurements that are derivative to the input dataset Additionally, the comparative data generated includes one or more of a generated image with a template, a generated image without a template, and a generated image compiled from multiple imaging modalities.

Another aspect of the disclosure is directed to a processor for use with a surgical navigation system used for spinal surgery wherein the processor is programmed to execute: receiving a pre-operative dataset and an inter-operative dataset, wherein each of the pre-operative dataset and inter-operative dataset comprises one or more medical images containing a spine region of interest as well as a dataset of location values associated with a four-point registration of each vertebral body visible within the spine region of interest; allowing a user of the surgical navigation system to specify an input dataset for each vertebral body pair within the spine region of interest; and rendering a block diagram of a spine, by using the four-point registration dataset from the input dataset selected by the user.

An aspect of the disclosure is directed to a machine readable medium means containing instructions stored on a non-transitory computer readable medium means that, when executed by a computing device means, cause the computing device means to perform a method, the method comprising: receiving an input dataset comprising one or more medical images containing a spine level of interest for a patient; and generating an optimized anatomical dataset for the spine level of interest wherein the optimized anatomical data set comprises one or more of a target disc height, a target anterior-posterior offset, and a target lordosis angle, and further wherein the step of generating an optimized anatomical dataset for the spine level of interest comprises the steps of: identifying zero, one or more visible spine levels in the one or more medical images to exclude from analysis; and accessing one or more image-derived measurements of a disc height measurement, an anterior-posterior offset measurement, and a sagittal lordosis angle measurement for one or more non-excluded spine levels; and applying a function to the one or more measurements from accessing one or more image-derived measurements to generate an optimized value for the spine level of interest for one or more of the target disc height, the target anterior-posterior offset, and the target lordosis angle. Additionally, the function can receive an input and applies one or more adjustments to correct for an assumed post-operative subsidence of an interbody device over time. In at least some configurations, the one or more adjustments is a disc height adjustment, an anterior-posterior offset adjustment, and a lordosis angle adjustment. The one or more medical images excluded from analysis can be excluded independently for one or more of an excluded disc height measurement, an excluded anterior-posterior offset, and an excluded sagittal lordosis angle. The function can also be one of an average function and a distribution function, and further wherein an input is selected from a medical literature. A surgical navigation system user may also specify a gross lordosis target for an entire region of a spine and wherein the function distributes one or more gross lordosis regional targets across a user-specified set of levels targeted for fusion surgery.

Another aspect of the disclosure is directed to a processor means for generating estimates of a weight carried at a spine level of interest, wherein the processor means is programmed to execute: accessing an input dataset for a patient comprising a weight of the patient, one or more image-derived measurements of a spatial relationships between two or more vertebral bodies visible within one or more images; allowing a user to specify a spine level of interest; and projecting an estimated weight carried at the spine level of interest by: looking-up one or more values from a previously published mass distribution function, wherein the mass distribution function comprises a set of percentage values associated with various bodily regions such that the sum of the set of percentage values equals 100%; summing x from the mass distribution function elements for all bodily regions cranial to a spinal region of interest; calculating y from the image-derived measurements of the spatial relationships between vertebral bodies from the input dataset, by determining an estimated percentage of the region of interest that is cranial to a spinal level of interest; summing x and y; and multiplying the sum of x and y by a weight of the patient to determine the weight carried at the spine level of interest. Additionally, the processor is configurable to calculate a sheer and a compressive component of the weight carried at the spine level of interest, using the image-derived measurements of the angulation between vertebral body endplates and a plumb line. In at least some configurations, the input dataset contains patient-specific data and wherein the computational routine incorporates a lookup function that returns a mass distribution which is a function of the patient-specific data. The patient-specific data can be selected from, for example, age, gender, and height. Additionally, the previously published mass distribution function is one selected by the user from among a set of available functions.

Still another aspect of the disclosure is directed to a processor means for use with surgical navigation system means used for spinal surgery wherein the processor means is programmed to execute: receiving an input dataset comprising one or more medical images containing a spine level of interest; and generating measurements of an operating range of the spine level of interest, comprising measurements of at least one of a minimum linear displacement between a pair of adjacent vertebral body corner-points from the spine level of interest and a maximum linear displacement between a pair of adjacent vertebral body corner-points from the spine level of interest by executing a computational process comprising: accessing one or more medical images containing the spine level of interest from the input dataset, and further accessing one or more measurements from each image of at least one of the minimum linear displacement and the maximum linear displacement; and applying at least one of a maximum function and a minimum function to the measurement sets to determine a maximum linear displacement value for a pair of adjacent corner points and a minimum linear displacement values for the pair of adjacent corner-points; and rendering data usable by a surgical navigation system based on the operating range measurements. The rendering of data usable by a surgical navigation system means can support a visual display means of the operating range measurements by the surgical navigation system means. Additionally, the data rendered can trigger an alert to a surgical navigation system user when the operating range measurement for the spine level of interest is outside of a user-determined threshold value.

Yet another aspect of the disclosure is directed to a processor means for use with a surgical navigation system means used for spinal surgery that wherein the processor means is programmed to execute: receiving an input dataset comprising one or more medical images, wherein each medical image includes an image of a spinal level of interest, one or more image-derived measurements for each medical image wherein the one or more image-derived measurements are selected from an alignment measurement, a lordosis measurement, a translation measurement, an angulation measurement, and a disc height measurement; allowing a user to specify a data presentation by selecting one or more of the image-derived measurements and by further selecting at least one of a minimum value and a maximum value; identifying a specific image view corresponding to the data presentation wherein an output of an identification process is a reference to an image that corresponds to the user specified data presentation; and generating comparative data between a current status of the patient wherein the generated comparative data uses a measurement from one or more image captured intra-operatively via the surgical navigation system and the data presentation. The measurement of interest can include measurements that are derivative to the input dataset. Additionally, the comparative data generated includes one or more of a generated image with a template, a generated image without a template, and a generated image compiled from multiple imaging modalities.

Another aspect of the disclosure is directed to a processor means for use with a surgical navigation system means used for spinal surgery wherein the processor means is programmed to execute: receiving a pre-operative dataset and an inter-operative dataset, wherein each of the pre-operative dataset and inter-operative dataset comprises one or more medical images containing a spine region of interest as well as a dataset of location values associated with a four-point registration of each vertebral body visible within the spine region of interest; allowing a user of the surgical navigation system to specify an input dataset for each vertebral body pair within the spine region of interest; and rendering a block diagram of a spine, by using the four-point registration dataset from the input dataset selected by the user.

INCORPORATION BY REFERENCE

All publications, patents, and patent applications mentioned in this specification are herein incorporated by reference to the same extent as if each individual publication, patent, or patent application was specifically and individually indicated to be incorporated by reference. See, for example, U.S. Pat. No. 8,676,293 issued Mar. 18, 2014 to Breen for Devices, systems and methods for measuring and evaluating the motion and function of joint structures and associated muscles, determining suitability for orthopedic intervention, and evaluating efficacy of orthopedic intervention; U.S. Pat. No. 8,777,878 issued Jul. 15, 2014, to Deitz for Devices, systems, and methods for measuring and evaluating the motion and function of joints and associated muscles and U.S. Pat. No. 7,502,641 issued Mar. 10, 2009, to Breen for Method for imaging the relative motion of skeletal segments

BRIEF DESCRIPTION OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

FIG. 1 illustrates two pairs of vertebral bodies which illustrates a normal pair and an offset pair;

FIGS. 2A-D illustrates a method for determining a target geometry for a spine surgery which allows a user to select a construct and provide for any exclusions (FIG. 2A), the vertebral bodies represented as rectangles illustrating PDH, ADH and offset (FIG. 2B), an image legend of maximum, current values, and minimum (FIG. 2C), and an application of the image legend to an exemplar pair of vertebral bodies represented by rectangles (FIG. 2D);

FIGS. 6A-B illustrate the Navigate functionality (a third function of the system);

FIG. 7 illustrates an exemplar screen for a Rothenfluh configuration;

FIG. 8 illustrates an exemplar screen for a Roussouly configuration;

FIGS. 9A-B illustrates sagittal alignment maps for Rothenfluh configuration and Roussouly configuration;

FIG. 10 illustrates an exemplar mark-up diagram;

FIG. 11 illustrates exemplar data for lordosis at a plurality of spinal levels;

DETAILED DESCRIPTION

Figure 3A:
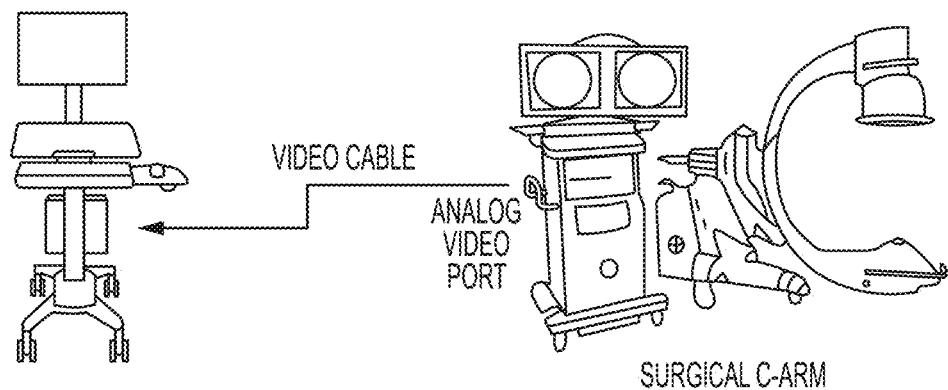
FIG. 3A illustrates a hardware diagram having a computer in communication with an analog video port and a surgical C arm.
Figure 3B:
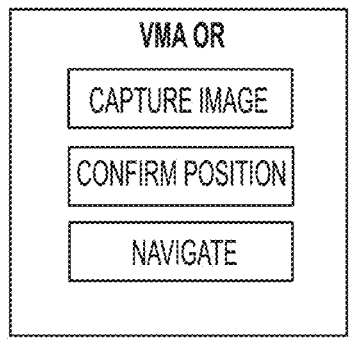
FIG. 3B illustrates a home screen for software.
Figure 4:
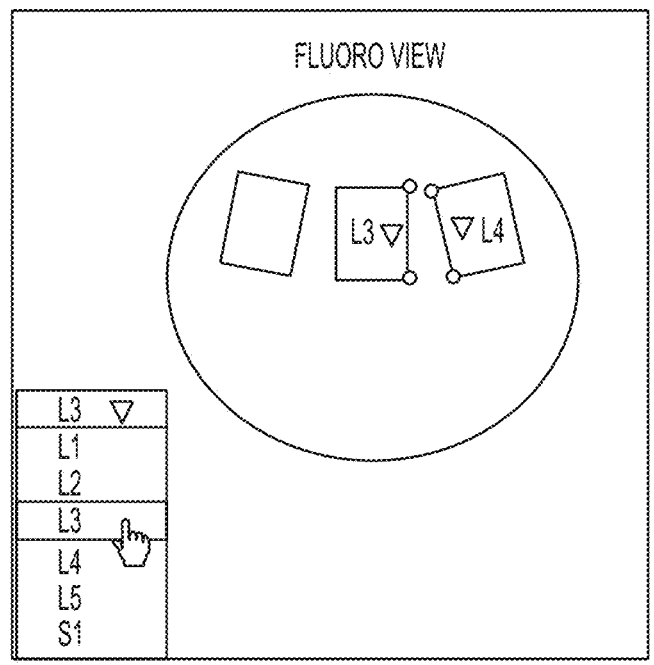
FIG. 4 illustrates the Capture Image functionality (a first function of the system)

One aspect of the present disclosure relates to a method for determining the target geometry of a spinal fusion surgical construct. Radiographic images of a patient's spine are acquired via any radiographic imaging method. From these images, specific measurements can be collected at levels not targeted for surgery from images collected while a patient is standing in a neutral position, including: anterior disc height, posterior disc height, offset (i.e. intervertebral translation), and/or angulation. These measurements are then used to generate a patient-specific average from the levels imaged but not targeted for surgery. These averages are then used to determine a set of target parameters for a surgical construct. These target parameters may then be used as the input to a surgical navigation system or may be used by the surgeon during surgery for device selection or to assist with the surgery. FIG. 1 illustrates two vertebral bodies in a current orientation and a target orientation with anterior disc height (ADH), posterior disc height (PDH) and offset.

As shown in FIGS. 2A-D a system user can select or exclude constructs for a plurality of vertebral pairs. For example, a patient targeted for surgery at L4/L5 may have lumbar spine radiographic images. Measurements of ADH, PDH, and Intervertebral translation (IVT) are then collected at Levels L1/L2, L2/L3, L3/L4, and potentially L5/S1, and averaged across these levels. These average parameters are the output of this method. The user may opt to delete specific levels from this average calculation, as shown in FIG. 2A.

Once these averages have been tabulated by the system, the user can view the resulting construct. The construct is as a series of points on a lateral and/or anterior-posterior projection of the anatomy. As will be appreciated the construct could also be a series of points on a 3D modality such as magnetic resonance imaging (MRI) or computed tomography (CT). These construct points may be manipulated by the user as shown in FIGS. 2B-D.

The data describing the target construct is created in a way that it is available for use by the surgical navigation system, having incorporated physician-specific assumptions as well as patient-specific data from prior diagnostic studies, such that it is unnecessary for any specific pre-surgical planning work step on the part of the surgeon. This workflow may incorporate image processing services that do processing of images and external reviews by radiologists. This workflow may also incorporate pre-rendered paper or pdf reports that allow target constructs parameters to be accessed by a user.

The system reduces workflow by enabling a user to determine whether a patient moves under a gravitational load of about 20%. Thus, when positioning a patient, the user can quickly determine whether it would be effective to attempt to get the level to open or reduce (i.e., is the level at its maximum mobility) Quantitative feedback provides assurance to the surgeons which results in increased definitive decision making in the operating room. Additionally, the systems is configurable to provide actionable new data. For example, the system can alert a user or surgeon when a "pharmaceutical reduction" is occurring. Information about, for example, a pharmaceutical reduction, can change a surgical decision from decompression to fusion. Additionally, the system is configurable with no touch constructs. Thus a surgeon can analyze the projected impact of different surgical constructions which takes into consideration, for example, implant size, anticipated subsidence, sheer and compressive loads, and PI-LL. The system also allows for confirmation of implant placement.

Once target construct has been determined, then intraoperative feedback systems can be used during surgery to assess current status of the geometry of a patient's spine surgery construct at a level or levels relative to the target construct's parameters as described above. This could be accomplished by having a fluoroscopic imaging device connected to a computer-mounted piece of frame-grabbing hardware configurable to digitize an image which could then undergo registration of the disc space on the image by a user (i.e., the space between two vertebral bodies in the spine). Once registered, this system would compare the registered image against the target and provide feedback to a surgeon user as to how much more a construct's geometry needs to be changed to achieve the target geometry. See FIGS. 3A-B, 4, and 6A-B.

This system is configurable to allow the user to incorporate various assumptions about levels of subsidence of device implants. This could mean that a target construct is sized to be larger than what is desired to be achieved post-operatively after patient recovery, so that after subsidence occurs the construct achieves the target construct geometry. This system is also configurable to allow the user to see the effects of the target construct on pre-operative parameters such as (Pelvic incidence minus lumbar lordosis) as well as the type of implant device dimensions that would be required to achieve the surgical construct. These parameters (target construct geometry, implant dimensions, projected forces, pelvic incidence minus lumbar lordosis, etc.) can all be changed dynamically, and when one parameter is changed the effect of the change is displayed for all other parameters. In addition the system can allow the user to configure a user-defined set of assumptions about the magnitude and distribution of projected subsidence. These assumptions could additionally be affected by surgeon input, such as the surgeon inputting data that the patient has osteoporosis or otherwise has bad bone quality, is obese, elderly, scoliotic, or other factors that could affect subsidence. Subsidence assumptions could be further personalized to a specific patient based on projected compressive gravitational loads across an implant. See FIG. 6A.

A second aspect of the disclosure is a method for determining the safe operating range of spinal joints during surgery. This method involves the use of a system that can assess the operating range of spinal levels (in terms of intervertebral rotation/angulation and translation) as an input device. Data for each level of the spine that has been measured is provided regarding the maximum and minimum observed rotation, translation, anterior disc height, and posterior disc height, as measured from a range of bending and load conditions. These ranges therefore represent the ranges to which spinal levels will go under voluntary movement conditions, which represents the sub-acute range with respect to potential ligamentous injury that could occur during spinal surgery due to external compressive or distractive forces applied by the surgeon during surgery. Such compressive and distractive forces are often applied during spinal surgery, during patient positioning when surgeons often attempt to induce maximum lordosis at a level, when determining the size and geometric/spatial configuration of the implant relative to the disc space, and when assessing of implanted hardware has been properly placed and configured. Image data from a previous diagnostic study could be available and accessible intraoperatively so a surgeon could selectively view the anatomy in specific positions, such as most lordotic, most kyphotic, most reduced, greatest anterior disc height, least anterior disc height, greatest posterior disc height, least posterior disc height, greatest opening to patient left, least opening to patient left, greatest opening to patient right, or least opening to patient right. See FIG. 6B.

This data about the minimum and maximum observed range of motion is then used with an intra-operative feedback systems to assess current status of the geometry of a patient's spine surgery construct at a level or levels relative to the minimum and maximum operating range of that joint (as described directly above). This could be accomplished by having a fluoroscopic imaging device connected to a computer-mounted piece of frame-grabbing hardware that could digitize an image which could then undergo registration of the disc space on the image by a user. Once registered, this system would compare the registered image against the minimum and maximum data and provide feedback to a surgeon user as to where the current anatomy is relative to its maximum and minimum demonstrated operating range. See FIG. 6A.

Figure 5A:
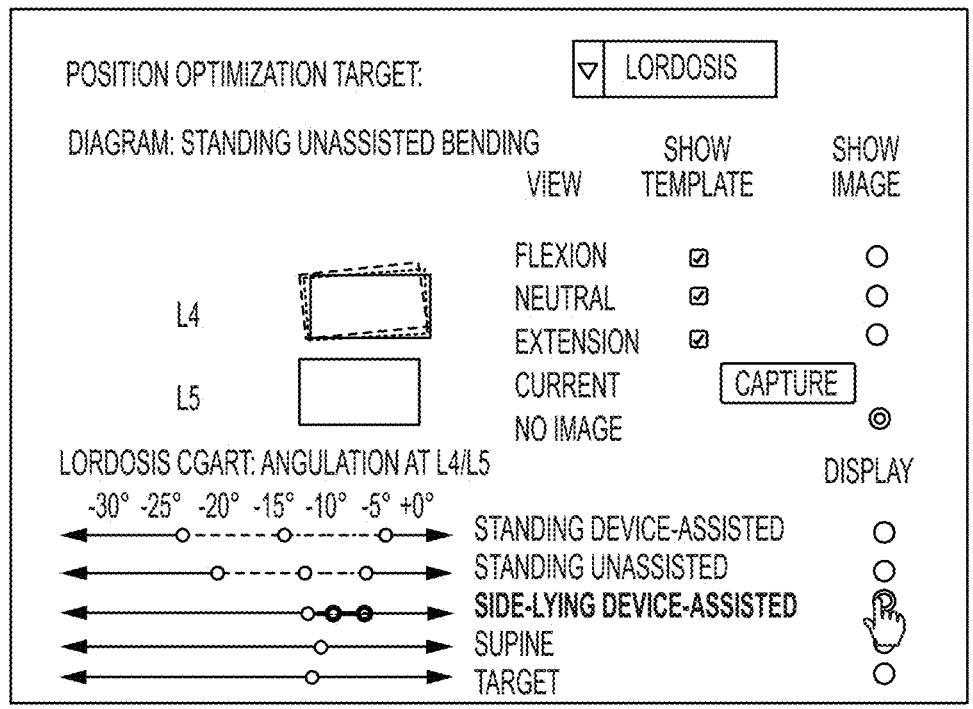
FIGS. 5A-C illustrate the Confirm Position functionality (a second function of the system)
Figure 5B:
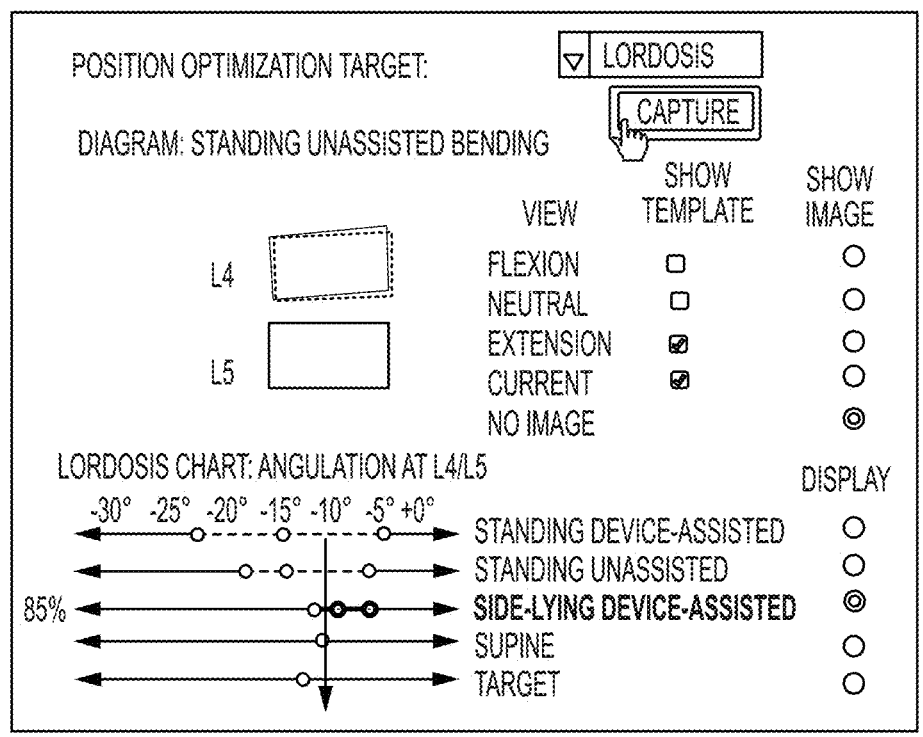
Figure 5C:
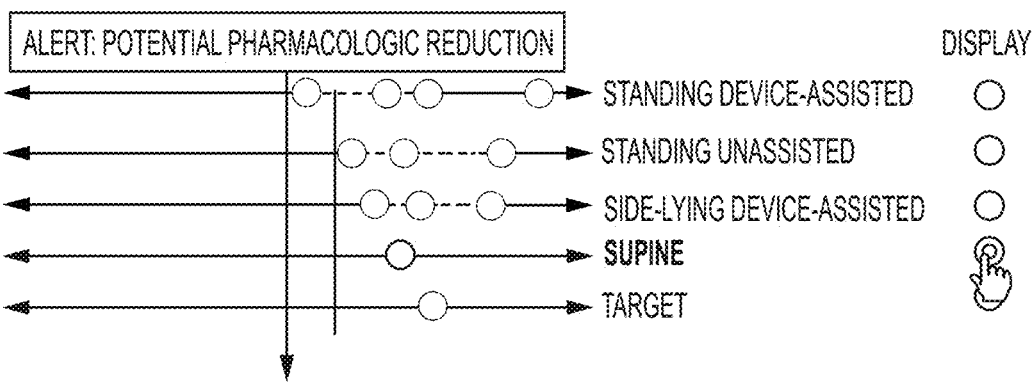
Figure 6B:
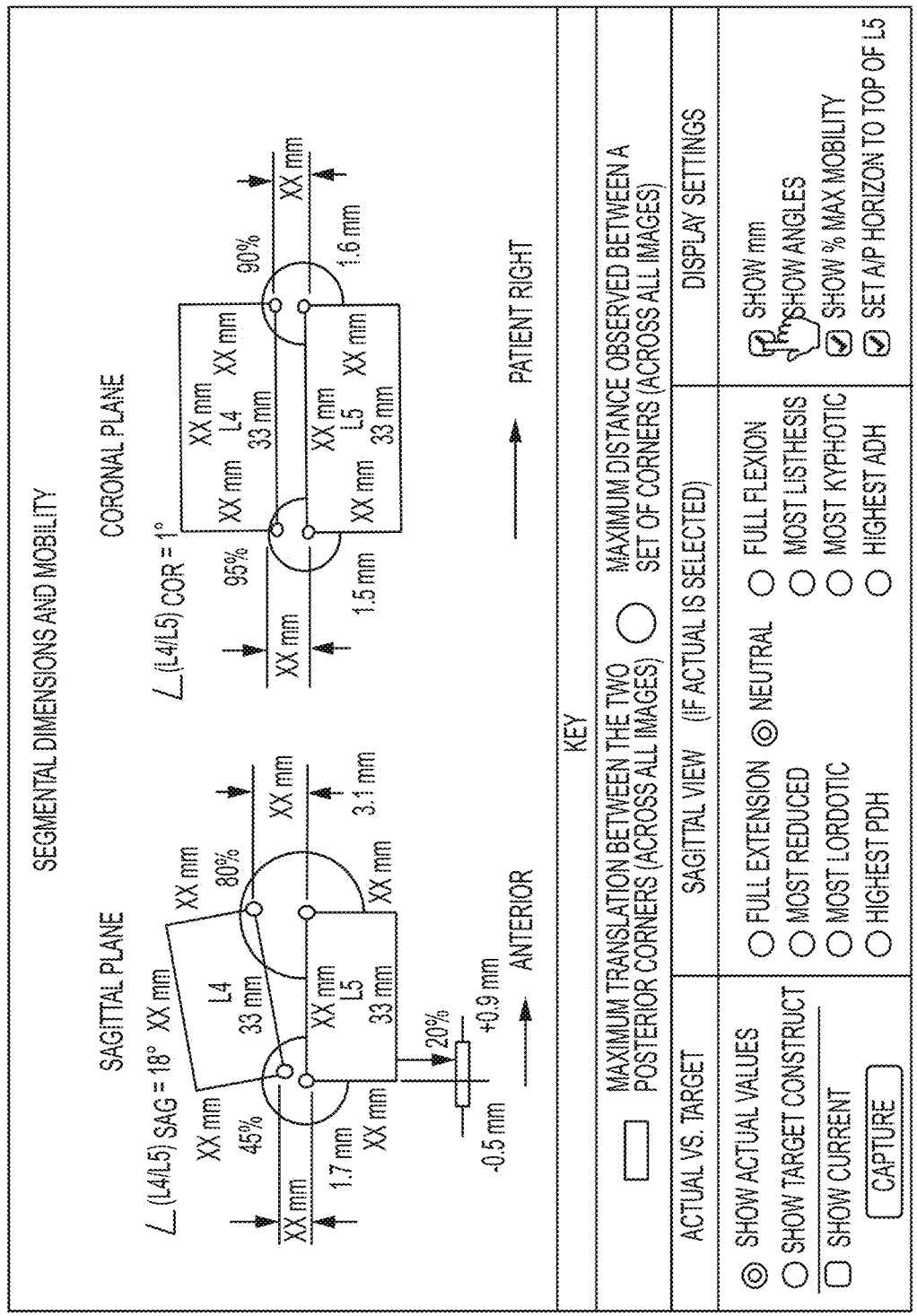

A third aspect of the disclosure includes a system for assisting with the positioning of a patient on an operating table prior to a surgery. Data from previous diagnostic studies of intervertebral motion would be available for comparison to a current position as captured using the frame grabber and fluoroscopic imaging device (as previously described). During patient positioning prior to surgery, the surgeon is often trying to achieve a specific position for a level targeted for spine surgery, such as maximum lordosis or most reduced. Using data from prior imaging studies along with a registered image taken during the patient positioning routine that occurs prior to surgery, the surgeon could compare a current position to the level's known range of operation to determine how much more positioning, if any, is required to achieve the target position for surgery. In the case that a patient that is anesthetized reduces more than has been observed on prior imaging studies, an alert could be triggered. See FIGS. 5A-C.

According to an embodiment of the disclosure, there is a lengthy requirements specification for a product that is capable of achieving the objects of the first through third aspects above, as well as other objectives. This requirements specification is provided in its entirety below, after which a fourth aspect of the disclosure is provided.

The systems can be summarized as having exemplar hardware features, and exemplar functional features.

Hardware Features:
The system can be IEC60601-compliant
The system can be a console mounted computer.
The system can have encrypted fixed media.
The system can allow for frame capture of an analog input from a surgical C-arm
The system can have the following hardware user interfaces: Mouse; Keyboard; USB Media port; Main monitor; Slave monitor.
The system typically does not include: External/network connectivity; or Touchscreen input capabilities
Functional Features: Overall Application:
The system can consist of an application that loads upon boot-up.
The system can be locked down, so that users can only access the system software application, and none of the resident functions within windows, unless a user presses a keystroke that will be known only to technicians.
The system can require a user to login using a username and password or a username and by answering security questions
The system can be shut down via user controls within the system Software.
Every screen of the software can feature a company or product logo, the system software version number, and the current date/time
There can be 3 major screens: Splash/Login Screen; Main Screen; Capture Screen
There can be one or more of the following modal windows: Load New Patient; Load Previous Session; Edit disc height (A1); Edit offset (A2); Edit Lordosis (A3); Lordosis Distribution Calculations, Rothenfluh (B1); Lordosis Distribution Calculations, Roussouly (B1); Edit Correction for Anticipated Subsidence (C1); and Calibrate (D)
Typically, there are be three main user types for the system:
  Surgeon: A surgeon can access any and all functionality of the system. The surgeon can access all previous patients saved to this system, and optionally (a site-level parameter) can open patients from any other surgeon who has saved cases to the system.
  OR Admin: The OR Administrator is an operating room administrator who can access any patient saved to the system and all functionality except making edits on the configuration screen (they can view, but not change the data).
  System Administrator: The System Administrator can change site level parameters and reset passwords for OR Admin and Surgeon users.
The input data for the system software is typically provided as an encrypted file to protect patient privacy that is accessed via USB media, and that was created by an online system as a rendered patient data package. See the "Input File Features" section for more details about this input file.
Functional Features: Data Saving and Storage
For each use session, the system can store one or more of at least:
  all actions taken by all users during all use sessions, excluding simple navigation. The actions that can be stored are defined as those that can affect any data structure within the system software system.
  a log a time/date/user stamp along with the action being taken.

the default configuration values associated with a surgeon user at the initialization of a use session, and changes to these configuration values made during the session.

the input data file.

The system can be configurable to recall any instance of a user session. This may be done by saving each instance before it is changed, or by storing sufficient data during each user session such that any instance of a user session can be reconstructed.

The system is also configurable to store each testing event in a first in, first out (FIFO) queue The queue system can use all allotted hard disc space, deleting older testing events first as more hard drive space is needed.

If and when the system is deleting older testing events, the system can present a message to the user prior to the deletion and allow the user to cancel the delete action.

The system is configurable to store the following information for each user:

Data associated with each ADMIN user including, Username, password, and password help questions.

Data associated with each SURGEON user including, User config variables, and acceptance status of the click through agreement, plus date/time of acceptance; and Username, password, and password help questions.

Site level parameters and data that gest stored:

The system is configurable to log all successful and unsuccessful login attempts.

Site configuration variable: Can Surgeons access patients created by other Surgeons?

To retrieve data from the system, the system is configurable to store data in such a way that it is accessible to a system trained technician by executing the technician Keystroke, then doing a manual copy of files from the system to removable media. This storage process can be fulfilled once a file structure exists that is accessible via the WINDOWS file explorer (or equivalent function) for copying to external media.

Functional Features: Video Frame Capture

The system is configurable to connect to an output port on a C-arm of the type DVI (capable of supporting both analog and digital signals). See. FIG. 3A.

Adapters can be used as needed or desired, to convert between DVI and other ports such as BNC, VGA, and others.

The system is configurable to:

Receiving a live video stream from the C-arm, for display by the software

Upon command, digitizing a current frame of the live video stream, and saving that image as a file that is usable by the software.

Splash/Login Screen:

Users can enter usernames, either by free text edit or by accessing a drop down list of existing user accounts that have been created on the system.

Users can enter a password or provide answers to security questions, in order to log into the system. Alternative means of authentication can be used without departing from the scope of the disclosure including RFID control, biometric data, and the like. Upon login:

If the user is a Surgeon type: check to see if: (1) the user typically has not been through the click throughs in the User Configuration pages, or (2) the user configuration pages have changed. If so, the user gets put into the configuration pages and can't progress to the Main Screen until the click through agreement has been agreed to.

The system can be capable of popping up the instructions for use (IFU) with click-through acknowledgement for the user's first login, and each time the IFU is updated.

The system is configurable to provide pop-up custom messages with a click-through acknowledgment, for assuring that all users are informed of updates such as release notes when software is updated and other messages.

Users can be able to create new user accounts.

Users can provide security questions and answers in the case that passwords cannot be remembered by the user.

Passwords can be resettable by system administrator users.

Users can be able to select "remember me", which will pull up the prior username upon initialization of the Splash/Login Screen Users may also initiate a shutdown Main Screen The Main Screen can be comprised of the following elements:

A first row of buttons (with User Manual, Load Patient, and Exit buttons)

A second row of buttons (with the Report, Capture, Calibrate, and Configure. In at least some configurations, the Report and Capture buttons can only appear after a patient has been loaded).

A left pane, which can assume three states

Sagittal Alignment Diagram

Lumbar View

Disc Space View

A right pane, which can assume two states:

Surgery Summary

Level Summary

With respect to how the left and right panes are displayed:

The initial default view (upon first coming to the Main Page) can be the Sagittal Alignment Diagram (left pane) and Surgery Summary (right pane).

The left and right pane can be independently changed by clicking a tab contained in a row of tabs at the top of each of the left and right panes.

The following can be visible and active to all users under all user scenarios:

On the first row of buttons:

Users can access an "Exit" button. Upon clicking the Exit button, users may be presented with the option to "Exit patient" (which puts user back on the surgery summary screen in its state when no patient has been loaded), "Logoff [USER]" (which puts the user back on the splash/login screen), and "Shutdown" (which initiates a shutdown sequences Users can also access a "Load Patient" button, which pops up the "Load New Patient" Modal Window. Prior to popping up the "Load New Patient" modal window, if an existing patient is loaded, user is warned that loading a new patient will close the current patient.

Users can be able to access a "User Manual" button, which pops up the current version of the user manual in a pdf viewer window.

On the second row of buttons:
Users can be able to access a "Calibrate" modal window by pressing a button
Prior to calibration there can be a ghosted, mismatched crosshair icon presented on the button.
After calibration there can be one sharp crosshair, and the label changes to "RECALIBRATE".
Users can be able to access a "Configure" button, that navigates the patient to the CONFIGURATION screen The following can be visible and active to all users once a patient has been loaded:
On the left pane of the window, there can be:
A series of tabs across the top section of the left pane. There can be seven tabs: "L1/L2", "L2/L3", "L3/L4", "L4/L5", "L5/S1", "Sagittal Alignment Diagram", "View Lumbar Images"
On each of the five tabs associated with the five lumbar levels, there can also be a check box and a label saying "Fusion?"
In the case that user config specifies the Roussouly method, then when the status variable [ADDITIONAL LORDOSIS FOR SA CORRECTION STATUS]="Not Confirmed" AND on the Surgery Summary object, the value in the "Additional Lordosis for Sagittal Alignment Corrections" edit box is not-zero, then:
the tab for each level ("L1/L2", "L2/L3", "L3/L4", "L4/L5", "L5/S1") can be inactive/ghosted, although the user can still be able to select a level for fusion for one of the levels (via the checkbox included in the tab).
There can be a prominent message to the user, with graphic objects such as arrows, that show that the user can either edit the value or press the OK button (these appear in the Surgery Summary in the middle section) to proceed to the Disc Space View. Without such messaging, the user may not have the knowledge as to why the tabs are ghosted and how to get to Disc Space View.
A main section of the left pane, which can be configured to contain one of three objects: Sagittal Alignment Diagram, Disc Space View, and View Lumbar Images. The user navigates to the three objects by selecting the appropriate tab (the tabs with the "L1/L2" "L5/S1" labels take the user to Disc Space View). Each of these three objects is described in a subsequent dedicated section of this document.
On the right pane of the window, there can be:
A series of tabs across the top section of the right pane. There can be three tabs: "Surgery Summary", "Level Summary", or "Capture".
A main section of the right pane, which can contain one of two objects: Surgery Summary Object or the Level Summary Object. The pane is selectable by the user by clicking one of the tabs.
If the user selects "Capture", then the "Capture" Screen can appear, which comprises a specific design for the left and right panes of the screen and is described in Detail in the "Capture" Section of this document.
If [ACTIVE LEVEL] is null, then the "Level Summary" tab can be inactive/ghosted. (see the Status Variable section of this document for more information about the [ACTIVE LEVEL] variable).

On the second row of buttons:
A "Report" button can be visible, which can pull up the report as a pdf document within a pdf viewer. The pdf viewer can occupy the entire window, and the only navigation available to the user at that point is "Done" and "Exit".
Once a user exits, if they re-open the viewer, it can automatically resume at the last page the user was looking at.
A "Capture" button can be visible, which can pull up the "Capture" Screen, which comprises a specific design for the left and right panes of the screen and is described in Detail in the "Capture" Section of this document.

Main Screen, Right Pane: Surgery Summary
There can be a matrix of objects, arranged as a table, which can include:
Row Labels for each level "L1/L2" "L5/S1"
A column of Checkboxes to specify a level for fusion
Specifying a level can check all three of the "exclude" boxes (from disc height, offset such that the two vertebra are not perfectly aligned, and lordosis calculations) associated with that level.
These check boxes can be synchronized with the fusion checkboxes on the tabs at the top of the left pane.
A column space direction to the right of the column of checkboxes that may display alert icons whenever alerts are activated for a given patient use session and for a specific level that has been selected for fusion surgery. The user can move the mouse over the icon mouse to present text appropriate with each activated alert. For more detailed features about the behavior of these alerts, see the "Alerts Features" section of this document.
A set of three columns of checkboxes labeled "Model Exclusions"
Deselecting the check box has no effect of the status of the checkboxes that indicate which levels are selected for fusion.
Each of the second and the third columns (Disc Height and Offset) can independently be either active or ghosted/inactive based on whether the value for the Disc Height and/or Offset status variable [CHECKBOX COLUMNS ACTIVE] is TRUE or FALSE (respectively).
For each row of checkboxes, selecting that row to receive fusion system can automatically select the three checkboxes. Deselecting the check box has no effect on the select/deselect status of the checkboxes that indicate a level is selected to receive fusion.
The three columns system can contain:
A column of Checkboxes to exclude a level from Lordosis calculations with the column header label "Lordosis"
A column of Checkboxes to exclude a level from disc height average calculations with the column header label "Disc Height"
A column of Checkboxes to exclude a level from offset average calculations with the column header label "Offset"
Edit button to edit Lordosis, that takes you to the "Edit Lordosis" (Modal window)
Edit button to edit disc height, that takes you to the "Edit Disc Height" (Modal window)

Edit button to edit offset, that takes you to the "Edit Offset" (Modal window)

A column of labels/dropdown labeled "Lordosis Data Source"

For levels that have not been selected for fusion, this can be a static label that can be visible for all levels For level that are selected for surgery, there system can a drop-down instead of just a label:

If there has not been a capture, then this is defaulted to "Target" and the values in the drop down are, for example, "Target", and other labels If they have undergone a capture, this is defaulted to capture and the values in the drop down can be "Capture", "Target", and other labels.

There can be a middle section, which system can assume one of two configurations, based on the user configuration selection of either the "Rothenfluh" or the "Roussouly" method for determining Sagittal Alignment corrections.

For users configured to the "Rothenfluh" selection, there can be:

A title label: "Edit/Confirm Additional Lordosis to Correct Sagittal Alignment"

A matrix of information:

A row of five labels: "Pre-Op", "Change vs Pre-Op: Segmental Lordosis (summed across all fusion levels)", "L1-S1 Sagittal Alignment Correction", "Correction for Anticipated Subsidence (summed across all fusion levels)", and "Post-Op"

Next to the "Change vs Pre-Op: Segmental Lordosis (summed across all fusion levels)" label, there can be an edit button that pops up the Edit Lordosis modal window.

Next to the "L1-S1 Sagittal Alignment Correction" label, there can be an edit button that pops up the appropriate modal window from the set (Lordosis Distribution Calculations, Rothenfluh B1; and Lordosis Distribution Calculations, Roussouly B2) based on the value in User Config.

Next to the "Correction for Anticipated Subsidence (summed across all fusion levels)" label, there can be an edit button that pops up the Edit Correction for Anticipated Subsidence modal window.

Underneath each label, there can be a value in degrees (rounded to the nearest whole number).

On the leftmost and rightmost of these values:
there can be a label "PI-LL=" to the left of the displayed values.
there can be space to display a single alert icon (either yellow or red) plus the short text "SA". For more detailed features about the behavior of these alerts, see the "Alerts Features" section of this document.

On the middle three of these values, the value is given as "+" or "−" a number to the left of the value.

On the value under the label "L1-S1 Sagittal Alignment Correction", there can be:
a single edit box with up/down increment buttons, which becomes active and non-null whenever at least one level is selected for fusion. See the "Calculations Features" section for the behavior of the variable in the edit box There can be an "OK" Button that is active whenever the edit box value is non-zero AND the status variable [ADDITIONAL LORDOSIS FOR SA CORRECTION STATUS] is set to "Not Confirmed" (See the Status Variable Features section of the document). Once either of these two actions is done, the OK button is invisible.

A label "Computed value based on default settings", along with the value in degree units rounded to the nearest whole number with either a "+" or "−" next to the number as appropriate.

FIG. 7 is a graphical representation of the features for the middle section for the "Rothenfluh" configuration:

For users configured to the "Roussouly" selection, there can be:

A title label: "Enter Any Desired Corrections to Upper/Lower Lumbar Arcs"

A simple diagram on the left side of the middle section:
A line angled to the angle of the superior edge of L1 in standing uncontrolled neutral, next to the label "L1"
A line with a label "Apex of lumbar curve" pointing to another label "LX" where "LX" is a variable set to the value of the apex of the lumbar curve (See the Calculations Features section for more information about the lumbar apex calculation).
A line angled to the angle of the superior edge of S1 in standing uncontrolled neutral, next to the label "S1".

A matrix of information, including:
A row of five column header labels: "Pre-Op", "Change vs Pre-Op: Segmental Lordosis (summed across all fusion levels)", "L1-S1 Sagittal Alignment Correction", "Correction for Anticipated Subsidence (summed across all fusion levels)", and "Post-Op"

Next to the "Change vs Pre-Op: Segmental Lordosis (summed across all fusion levels)" label, there can be an edit button that pops up the Edit Lordosis modal window.

Next to the "L1-S1 Sagittal Alignment Correction" label, there can be an edit button that pops up the appropriate modal window from the set (Lordosis Distribution Calculations, Rothenfluh B1; and Lordosis Distribution Calculations, Roussouly B2) based on the value in User Config.

Next to the "Correction for Anticipated Subsidence (summed across all fusion levels)" label, there can be an edit button that pops up the Edit Correction for Anticipated Subsidence modal window.

Two row header labels: "Upper Arc" and "Lower Arc".

A 5×2 array of data, showing values in degree units, rounded to the nearest whole number/
On the middle three of these values, the value is given as "+" or "−" a number to the left of the value.
For the two values in the column labeled "L1-S1 Sagittal Alignment Correction", these can be edit boxes with up/down increment buttons.

The defaulted value can be zero

If no levels are selected for surgery in the upper arc, then the upper arc edit box can be ghosted and not editable. The same system can apply to the lower arc edit box.

A row of information, with the label "Lordosis Type", with the lordosis type underneath both the "PRE-OP" and "POST-OP" columns, and being able to assume the values 1, 2, 3, or 4.

A row of information, with the label "Pelvic Tilt", with the Pelvic Tilt value underneath both the "PRE-OP" and "POST-OP" columns, and being a value in degree units that is rounded to the nearest whole number.

There can be two spaces, each one able to show a triangle icon, either yellow or red, plus the short text "SA". Each alert icon/short text is horizontally spaced next to the each of the two columns of data associated with "Lordosis Type" and "Pelvic Tilt" (as described directly above), and vertically spaced between those two rows. See the "Alerts Features" Section for more specification about the conditions that various alerts become active.

FIG. 8 is a graphical representation of the features for the middle section for the "Roussouly" configuration:

Main Screen, Right Pane: Level Summary

In the case that the [ACTIVE LEVEL] is not selected for fusion, there can be no visible objects in this panel. (note: See the section Main Screen for more info about the [ACTIVE LEVEL] variable).

In the case that the [ACTIVE LEVEL] is selected for fusion, there can be two sub-panels: An upper sub-panel for Surgical Considerations and lower one for Lordosis Analysis:

The upper sub-panel for Surgical Considerations system can:

Have a label which says "[ACTIVE LEVEL] Surgical Considerations"

Display up to three alerts, each one comprising an icon and alert text. See the Alerts Features section of the features document for more details about features for these alerts.

The lower sub-panel for Lordosis Analysis system can:

Have a label which says "[ACTIVE LEVEL] Lordosis Analysis"

There can be a matrix of values, comprising:

A row of four column heading labels: "Expected Lordosis @ [ACTIVE LEVEL]", "Sagittal Alignment Correction", "Correction for Anticipated Subsidence*", and "Segmental Lordosis Target".

Next to the "Expected Lordosis @ [ACTIVE LEVEL]" label, there can be an edit button that pops up the Edit Lordosis modal window.

Next to the "Sagittal Alignment Correction" label, there can be an edit button that pops up the appropriate modal window from the set (Lordosis Distribution Calculations, Rothenfluh B 1; and Lordosis Distribution Calculations, Roussouly B2) based on the value in User Config.

Next to the "Correction for Anticipated Subsidence*" label, there can be an edit button that pops up the Edit Correction for Anticipated Subsidence modal window.

Underneath the column headers, in the second through the fourth column can be an editable text box, arranged in a row beneath the row of column headings, with up/down increment buttons, and defaulted to the computed value. This row can have the row heading of "Target Construct"

In that same row, underneath the column header in the first column, there can be a value for expected Lordosis at [ACTIVE LEVEL].

Underneath the "Target Construct" row described above, there is another row of degree values (#°, one for each column, with the row heading of "Computed Values based on default settings."

See "Calculation Features" section for more details about the values that are displayed in these boxes.

Underneath the "Computed Values" row, aligned with the "Correction for Anticipated Subsidence" column, there can be a label for "Maximum Anticipated Anterior Subsidence*", and underneath that there can be an editable text box with up/down increment buttons and containing a value in millimeter units (#.# mm).

There can be a label in red next to the editable text box "Maximum Anticipated Anterior Subsidence" that says "Default value was adjusted down because gravity is acting nearly parallel to the level". This label only appears if there has been an automatic reduction to the default MAAS value (see the Calculation Features section for more details about the conditions when this can occur).

There can be a label at the very bottom of the panel that displays a note explaining what is meant by the asterisk next to the labels "Correction for Anticipated Subsidence*" and "Maximum Anticipated Anterior Subsidence*". That label system can say "*This estimate of potential lordosis loss due to subsidence is a geometric calculation based on the individual vertebral body dimensions of each patient. This calculation uses an assumed "Maximum Anticipated Anterior Subsidence" which represents the upper end of expected subsidence. Consider adjusting upward from the default value when patient has poor bone quality or when interbody device placement is posterior. Consider adjusting downward from the default if the level receives anterior fixation or when interbody device placement is anterior."

See "Calculation Features" section for more details about the values that are displayed in these boxes, including the default values and how these values change.

Main Screen, Left Pane: Sagittal Alignment Diagram

There can be block diagrams of the anterior column of the spine, based on the coordinates of each vertebral body from the standing uncontrolled neutral view.

The diagram can be updated with any change to:

The set of levels selected for fusion.

The lordosis data source specified at a level

The target construct geometry, for levels specified to draw lordosis data from the target construct. Target construct geometry can be changed by a number of user actions. Any of the items that can change the target construct can also therefore trigger an update to the Sagittal Alignment diagram.

A capture, for levels specified to draw lordosis data from a capture

Each vertebral body can be labeled

The femoral head can be represented by two circles.

There can be the following lines overlaid:
A. A line along the top of L1
B. Two diagonal lines overlaid on L1, connecting opposing corners
C. A line perpendicular to A that intersects with the intersection of the diagonal lines in B, and extends to the intersection of E
D. A line along the top of S1
E. A line perpendicular to D that intersects D at the midpoint of the upper edge of S1.
F. A line connecting the center points of the femoral head circles.
G. A line originating at the midpoint of F and extending to the intersection of D and E.
H. A line originating at the intersection of D and E extending along the horizontal.
I. A line originating at the midpoint of F and extending upward along the plumb line.
J. Labels: PI, PT, SS, and LL.

There can be a vertical plumb line, with a label: "Gravity"
 The Sagittal Alignment Diagram can be oriented such that the plumb line aligns with the vertical axis of the page.

There can be a matrix of data:
 Row Labels: "LL=", "SS=", "PI=", and "PT="
 Values can be presented next to each label, in degree units rounded to the nearest whole number.

For users that are configured for the "Rothenfluh" method for determining Sagittal Alignment corrections, the additional following objects can be present in the Sagittal Alignment Diagram:
 There can be a label at the bottom "PI-LL=", along with the PI-LL Value
  There can be space to show a single triangle icon, either yellow or red, plus short text, based on whether or not the Sagittal Alignment alert is activated. See the "Alerts Features" Section for more specification about the conditions that various alerts become active.
 There can be a label "Lordosis Type X (Roussouly)", wherein the "X" is the Roussouly Type, and can assume the value 1, 2, 3, or 4. See the Calculations Features section for more information about the function to determine the Roussouly Lordosis Type.

For users that are configured for the "Roussouly" method for determining Sagittal Alignment corrections, the additional following objects can be present in the Sagittal Alignment Diagram:
 There can be a label "Lordosis Type X (Roussouly)", wherein the "X" is the Roussouly Type, and can assume the value 1, 2, 3, or 4.
 There can be a label "Pelvic Tilt" as well as the pelvic tilt value given in degree units rounded to the nearest whole number.
 There can be space to show a single triangle icon, either yellow or red, plus short text, horizontally spaced next to the two values associated with "Lordosis Type" and "Pelvic Tilt" (as described directly above), and vertically spaced between those two rows. See the "Alerts Features" Section for more specification about the conditions that various alerts become active.
 A Label that says "APEX" positioned next to the appropriate vertebral body label. [NOTE: In some prior designs, this was the "APEX" label plus an arrow pointing to a vertebral body. This design was abandoned, as the arrow could confuse the user into thinking that the APEX is at a certain point within the vertebral body height, as opposed to simply identifying the vertebral body in which the apex occurs.]
 Additional data elements positioned underneath the "Lordosis Type X (Roussouly)" label described above: "Total L1-S1 Lordosis=X°", "Upper Lumbar Arc=Y°", and "Lower Lumbar Arc=Z°"

FIGS. 9A-B for the Rothenfluh and Roussouly versions of the Sagittal Alignment Diagram:

Main Screen, Left Pane: Disc Space View

The Disc space view corresponds to the [ACTIVE LEVEL] level (i.e. it presents data about the [ACTIVE LEVEL]

On the left hand pane of the widow: there can be four sub-panels: (1) An upper left sub-panel (for the disc space diagram), (2) an upper right sub-panel (for the Distance From/To diagram), (3) a middle sub-panel (for the data table sub-panel), and (4) a lower sub-panel (for overlays/options.

In the upper left sub-panel, which is for the Disc Space Diagram, there can be:
 A title label "Disc Space View"
 A check box that makes the Disc Space Diagram visible and un-visible (respectively). This comes defaulted to visible.
 The Disc Space Diagram (the features for the Disc Space Diagram are given below in a separate dedicated sub-section below)

In the upper right sub-panel, which is for the Distance From/To Diagram, there can be:
 There can be:
  A label that says "Distance From [DROP DOWN 1] to [DROP DOWN 2]"
  [DROP DOWN 1] system can:
   Allow users to select from the list:
    Current Capture: If [CAPTURE STATUS] is not "No Capture Yet", else this is ghosted
    Reference View (may be visible)
    Target Construct: if [ACTIVE LEVEL] is selected for fusion, otherwise this is ghosted/inactive.
    Prior Captures: if [CAPTURE STATUS] is "Current Capture with Prior captures",
     THEN there is a prior captures section, with the header "Prior Captures", along with a list of prior captures, as specified in the Status Variable Features Section (see the end of the [REFERENCE VIEW] section)
     ELSE there is only the label "Prior Captures" that is ghosted/inactive
    If an line item is selected on [DROP DOWN 2], then that line item is ghosted on [DROP DOWN 1] (and vice versa)
   Be defaulted to:
    "Current Capture" in the case that the [CAPTURE STATUS] is not "No Capture Yet"
    ELSE "Reference View"
  [DROP DOWN 2] can have the same rules as [DROP DOWN 1], except for:

Allows users to select from the list:
All items the same as for [DROP DOWN 1], except that the value (null) can be allowed in [DROP DOWN 2].
Default values can be:
"Target Construct" in the case that the if [ACTIVE LEVEL] is selected for fusion
ELSE null
A checkbox next to the above-described label, such that checking and unchecking the check box makes the Distance From/To diagram object visible and un-visible (respectively). This comes defaulted to visible.
The Distance From/To Diagram (the features for the Distance From/To Diagram are given below in a separate dedicated sub-section below)

In the middle sub-panel, which is for the data table, there can be:
A Label that says "Dimensions"
A drop down box with a label saying "Linear Dimension Units", with a drop down box that is defaulted to the user configured default, and which can assume the values of millimeters, % Vertebral Body Depth, % Max Range.
The following columns: Posterior Disc Height, Midline Disc Height, Anterior Disc Height, Segmental Lordosis, PI-LL
On the PI-LL column, if there are PI-LL alerts that have been activated, a yellow or red (as appropriate) alert icon can be displayed next to the appropriate number.
There can be a row for Target Construct, Current Capture, and Reference View, so long as the respective check box in the "Overlays" section is selected. In the case that the checkbox is not selected, then the row system cannot appear, and the table will be shorter.
In the case of Reference View, row heading can be "Ref. View: [VIEW TEXT]". See the Status Variable features section for more information about the Reference View variable.

In the bottom sub-panel, which is for the Overlays and Options, there can be:
A Label that says "OVERLAYS"
Underneath the "OVERLAYS" label, checkboxes and icons for: Target Construct, Current Capture, Reference View, Mobility Ranges, and Gravity (plumb).
For Target Construct, it can be ghosted/inactive if [ACTIVE LEVEL] is NOT selected for fusion.
For the Current Capture row, there can be two configurations:
If [CAPTURE STATUS]="Current Capture with no prior captures", then there can be a label saying "Current Capture" (not a drop down).
If [CAPTURE STATUS]="Current Capture with prior captures", then there can be a drop down, defaulted to the Current Capture, which draws from the list comprised of the Current Capture plus the Prior Captures, as described in the Status Variables Section of this document (see the end of the Reference View part of that).
If [CAPTURE STATUS]="No capture yet", the row (including the label, icon, and checkbox) can be ghosted.
For the Reference View row, there can be a drop down underneath which has a drop down box that allows the user to select among the [REFERENCE VIEW] values (See section about the Reference View in the Status Variable features section of this document for more details about these potential values)
A Label that says "OPTIONS"
Underneath the "OPTIONS" label:
A checkbox that says "Images" such that checking and unchecking the check box makes the image underlays visible and invisible (respectively).
Indented from the checkbox above, a set of three radio buttons with the labels "Target Construct", "Current Capture", and "Reference View", defaulted to the value specified in user config, such that the specific image view is switched when the radio button values change.
Items in the set of three radio buttons ("Target Construct", "Current Capture", and "Reference View") are ghosted/inactive if the corresponding checkbox in the "OVERLAYS" section is deselected, and become active when the corresponding checkbox is selected
A checkbox that says "Labels"
Checkbox, radio button, and drop down default values can be set as configured in the user configuration variables. Once a user selects/deselects checkboxes and radio buttons or changes the value in dropdowns in this section, those values system can persist if the user should go to view another level's disc space view, or if the user goes to another screen and then returns.

The Disc Space Diagram can be a diagram that, when activated for display, will occupy the upper left sub-panel of the left pane of the Disc Space View screen, and system can contain:
A target construct outlined in blue that is selectably visible (based on the checkbox value):
A target construct, inferior vertebral body, positioned such that the superior edge aligns with the horizon, and that incorporates are "balls" at each of the superior anterior and superior posterior corners.
A target construct, superior vertebral body, that incorporates are "balls" at each of the inferior anterior and inferior posterior corners
The target construct, superior vertebral body object described above system can only be visible if the [ACTIVE LEVEL] is selected for fusion. In all other cases, the object is invisible.
A capture outlined in red, that is selectively visible (based on the checkbox value):
A capture, superior vertebral body
If [CAPTURE STATUS] is equal to "No Capture Yet" the current capture, superior vertebral body system cannot be displayed.
If the user has selected a prior capture from "OVERLAYS" Section, the box should be red, but a different hue that is darker (as compared to red used for the current capture)
A reference view outlined in green, that is selectively visible (based on the checkbox value):
A reference view, superior vertebral body
A set of min/max mobility range graphic elements that are selectably visible (based on the checkbox value)
A posterior mobility range graphic element, which is:
a vertical element that has a background line that goes through the superior posterior corner of the target construct, inferior vertebral body, and also has a vertically oriented elongated rectangle (the long axis superimposed on the background line) that is sized to represent the min/max mobility range of the posterior disc height (PDH).
    This element stays fixed in space if/when the user moves or rotates the target construct, superior vertebral body.
  A horizontal background line that goes through the inferior posterior corner of the target construct, superior vertebral body, which meets the vertical element, and then becomes an arrow (on the other side of the vertical element) pointing to the vertical element.
    This element moves along with the target construct if/when moves or rotates the target construct, superior vertebral body.
A vertical anterior mobility range graphic element, which is
  a vertical element that has a background line that goes through the superior anterior corner of the target construct, inferior vertebral body, and also has a vertically oriented elongated rectangle (the long axis superimposed on the background line) that is sized to represent the min/max mobility range of the anterior disc height (ADH).
    This element stays fixed in space if/when the user moves or rotates the target construct, superior vertebral body.
  A horizontal background line that goes through the inferior anterior corner of the target construct, superior vertebral body, which meets the vertical element, and then becomes an arrow (on the other side of the vertical element) pointing to the vertical element.
    This element moves along with the target construct if/when moves or rotates the target construct, superior vertebral body.
A horizontal offset mobility range graphic element, which is:
  a horizontal element that has a background line that goes through the superior posterior corner of the target construct, inferior vertebral body, and also has a horizontally oriented elongated rectangle (the long axis superimposed on the background line) that is sized to represent the min/max mobility range of the offset.
    This element stays fixed in space if/when the user moves or rotates the target construct, superior vertebral body.
  A vertical background line that goes through the inferior posterior corner of the target construct, superior vertebral body, which meets the horizontal element, and then becomes an arrow (on the other side of the horizontal element) pointing to the horizontal element.
    This element moves along with the target construct if/when moves or rotates the target construct, superior vertebral body.
A plumb line gravity indicator arrow that is selectively visible (based on the checkbox value), with an arrow endpoint that is co-located with the midpoint of the inferior edge of the target construct, superior vertebral body.

Background images (underlays) that are selectively visible (based on the checkbox value). User can select to have background images underlays be visible or invisible.
  Users can further can specify to select from a set of three radio buttons with labels "Target Construct", "Current Capture", and "Reference Views".
    If [CAPTURE STATUS]="No Capture Yet", then the "Current Capture" can be ghosted/inactive.
    If the [ACTIVE LEVEL] is not selected for fusion, then the "Target Construct" is ghosted/inactive
  If Reference View or Current Capture are selected, the appropriate image is displayed. These Images (all reference views and the current capture) can have been cropped to the [ACTIVE LEVEL]:
    Find the leftmost, rightmost, topmost, and bottom most coordinates from the 8 points (4 for superior vertebral body, 4 for inferior vertebral body.
    Extend 10% in each direction. [Note: This is a guess. This needs to be played with a bit to see what looks the best.]
    Crop a square region around the two vertebral bodies, oriented to align the superior edge of the target construct, inferior vertebral body. (note1: If it is not too processor intensive, smooth/fade the borders. Note2: the cropped regions should be the same across views in terms of the cropping relative to the inferior vertebral body of a level, so that switching the image to view does not change the shape of the image underlay)
  In the case the user has selected Target Construct, a view is rendered:
    Use as a base image the cropped standing neutral uncontrolled view. In the case that a current capture has occurred, use as a base image the cropped current capture image.
    Cut the image along the inferior edge of the superior vertebral body.
    Rotate and translate the upper section (above the cut) to position it where the target construct is positioned.
      Allow the upper section to overwrite the lower section of the images.
      If new space is created, that space can be filled with pixels colored to the average color across the image.
      Re-Apply the cropping parameters
  In the case the [ACTIVE LEVEL] is newly selected for fusion surgery AND from the User Config the default image is set to "Target Construct", then switch the image being viewed to Target Construct (and update the radio button) from whatever its current value is.
  In the case the status variable [CAPTURE STATUS] changes from "No Capture Yet" to any other value AND from the User Config the default image is set to "Current Capture", then switch the image being viewed to Current Capture (and update the radio button) from whatever its current value is.
The following actions can be available to the user when moving the mouse over specific regions of the Disc Space Diagram:
  The Target Construct, Superior vertebral body can be able to be grabbed and moved/rotated:
    Grab/Drag the inferior edge of the target construct, superior vertebral body, and the user can be allowed to translate the target construct, superior vertebral body up/down and left/right.

Grab/Rotate the "balls" of the inferior edge of the target construct, superior vertebral body, and the user can be able to change the angle of the target construct.

Max range of motion allowed for Gmb/Drag and Grab/Rotate actions: All points of the target construct, superior vertebral body system can stay within a rectangle with horizontal edges parallel to the superior edge of the target construct, inferior vertebral body, defined by:

Left/right: Max of [leftmost/rightmost points (among the 8 points for each view) across all Reference views, extending 10% beyond in each direction] OR 50% of vertebral body depth on either side Up: 200% of Inferior vertebral body midline height above the horizontal superior edge of the Target Construct, inferior vertebral body.

Down: Minimum of the cropped regions across all Reference Views

In the case that: (1) image underlays are selected to be visible, and (2) the target construct is selected as the view to display;

then upon any update to the position/angle of the target construct, superior vertebral body, the target construct view needs to be re-rendered based on the updated location/angle.

This update also system can occur whenever the target construct geometry is updated by any other mechanism (see Calculation Features for all of the situations in which the target construct geometry is changed).

In the case that the Distance From/To diagram is visible, then upon any update to the position/angle of the target construct, superior vertebral body, the Distance From/To Diagram view needs to be re-rendered based on the updated location/angle.

Click the Plumb line gravity indicator arrow, and the Disc Space Diagram can be rotated such that the plumb line aligns with the vertical axis of the screen. Clicking the plumb line again will re-orient the Disc Space Diagram such that the target construct, inferior vertebral body's superior edge is parallel to the horizontal axis of the screen.

The Distance From/To Diagram can be a diagram that, when activated for display, will occupy the upper right sub-panel of the left pane of the Disc Space View screen, and system can contain:

Three boxes can be displayed: The "from" construct, inferior vertebral body; the "from" construct, superior vertebral body, and the "to" construct, superior vertebral body (filled in and on top of the other boxes)

These boxes can be vertically positioned such that they align with the Disc space View graph to the left.

Each box system can assume the appropriate color as already defined (blue=target, red=current capture, green=reference). For a prior capture, the box should be red, but a different hue that is darker (as compared to red used for the current capture).

In the case that [DROP DOWN 2] is NOT null, then three red arrow objects (and associated text and alert icons) can be placed on the diagram, relative to box associated with the "from" construct, superior vertebral body.

Each of the arrows can be sized commensurate with the associated value

Each associated value can be displayed near the arrow in the format "#.# mm"

There can be:
  A posterior height arrow
    In the case that the value is an upward (positive) or zero value, the arrow can be positioned relative to the posterior inferior corner of the current capture box.
    In the case that the value is a downward (negative value), the arrow can be positioned relative to the posterior superior corner of the current capture box.
    In the case that an alert SP or PSO (or both) is active, there can be the appropriate alert icon displayed next to the value text associated with the posterior height arrow.
  An anterior height arrow
    In the case that the value is an upward (positive) or zero value, the arrow can be positioned relative to the anterior inferior corner of the current capture box.
    In the case that the value is a downward (negative value), the arrow can be positioned relative to the anterior superior corner of the current capture box.
    In the case that an ALL alert is active, there can be the appropriate alert icon displayed next to the value text associated with the anterior height arrow.
  An offset arrow
    In the case that the value is a rightward (positive) or zero value, the arrow can be positioned relative to the posterior inferior corner of the current capture box.
    In the case that the value is a leftward (negative value), the arrow can be positioned relative to the anterior inferior corner of the current capture box.
  A rotation indicator icon along with a text label showing the additional lordosis
    The additional lordosis value can be displayed near the icon in the format "+#°" or "−#°" as appropriate based on the value.
    The icon can be a counterclockwise rotation icon in the case that the additional lordosis value is positive or zero.
    The icon can be a clockwise rotation icon in the case that the additional lordosis value is negative.

Main Screen, Left Pane: View Lumbar Images

There can be a title label: "Reference View", with a drop down box referencing the REFERENCE VIEW variable.

There can be a space on the page for the image to reside in its native format (Optimized for 1 k×1 k pixels, but able to accept up to 2 k×1.5 k).

There can be a gravity Indicator, comprising an arrow and a label "Gravity" next to the image, that is selectably visible (based on the checkbox), but also that system can only be visible if the [REFERENCE VIEW] has gravity data (otherwise this object is invisible).

Underneath the image, there can be the following user input sections:

A column title label "ORIENTATION", under which is a set of radio buttons corresponding to the labels "Gravity", "Most Recent Capture", "Native" or "LX Superior Edge"
    "LX" can be the vertebral body label corresponding to the ACTIVE LEVEL.
    The "LX Superior Edge" item (Label+radio button) can be invisible and inactive if there is ACTIVE LEVEL=null.
    The "Most Recent Capture" item (Label+radio button) can be inactive/ghosted if the [CAPTURE STATUS]="No Capture Yet"
    The "Gravity" item (Label+radio button) be inactive/ghosted if the [REFERENCE VIEW] does NOT contain gravity data.
    This set of radio buttons can be defaulted based on data from user config, and whenever a new value is selected, the image and the gravity indicator get rotated as appropriate.

A column title label "SELECT VIEW", under which is a set of radio buttons corresponding to the labels "LX-LY", "LY-LZ", or "Pelvic View"
    The two elements "LX-LY" and "LY-LZ" appear in this list only if there are both superior and inferior views associated with a specific REFERENCE VIEW. If there is only one view that contains L1-S1, then there will only be one label "L1-S1".
    The "Pelvic View" item will only appear if REFERENCE VIEW=Standing uncontrolled neutral.
    This section (the column titled "SELECT VIEW") can be invisible if there is only one item (i.e. "L1-S1", meaning no superior/inferior views and no pelvic view).

A column title label "OPTIONS", under which is a set of check boxes corresponding to the labels "Gravity", "Labels" and "Templates"
    Selecting/Deselecting the "Gravity" checkbox makes the gravity indicator described above toggle between visible/invisible (respectively).
        The "Gravity" item (Label+checkbox) be inactive/ghosted if the [REFERENCE VIEW] does NOT have gravity data.
    Selecting/Deselecting "Labels" makes the vertebral body label overlays on the image toggle between visible/invisible (respectively).
    Selecting/Deselecting "Templates" makes the vertebral body template overlays on the image toggle between visible/invisible (respectively).
        Templates get created via a function that creates corner and cross hairs line coordinates, provided a 4 (x,y) vertebral body position corner points. [This function can be achieved using Matlab from MathWorks® However, other languages can be used without departing from the scope of the disclosure.].

Capture Screen

The Capture Screen can be substantially the same as the Main Screen. Whereas the Main Page has three variants on the left pane and two on the right pane, the Capture Screen represents a variant of the left and right pane can be displayed together.

The left pane system can: Contain the following page elements:
A title label "Fluoro View"
Underneath title, there can be set of five radio buttons, with labels "L1/L2" . . . "L5/S1", arranged in a row, with that row header labeled "Level to Capture", and which are linked to the value of [MARKUP LEVEL]
    This can be defaulted to [ACTIVE LEVEL], and can be changeable by the user.
    In the case that [ACTIVE LEVEL]=null, then this row of radio buttons is active, but none are selected.

There can be an Image Section wherein image system can reside in its native format (Optimized for 1 k×1 k pixels, but able to accept up to 2 k×1.5 k).

There can be a set of labels and radio buttons, this set of labels and radio buttons being labeled "VIEW:"
    "Live Fluoro Feed", when selected, system can show in the image space the live fluoro feed coming from the image capture system.
    "Live Fluoro Feed" is the default value. Until a capture has occurred, this set of radio buttons can only have the value "Live Fluoro Feed"
    "Current Capture", when selected, system can show the image stored as the current capture.
        If [MARKUP STATUS] is equal to Step 0 to Step 4 (i.e. not step 5), then the previously marked up corners can be visible on the image, and available for editing by the user.
    In the case that a [CAPTURE STATUS] is set to "Current Capture with Prior captures", then there system can also be the item "Prior Capture" visible, which can be positioned next to a drop down list populated by a list of the prior captures. The specific features for the list of prior captures for the drop down list can be found in the section about the status variables [REFERENCE VIEW] and [COMPARE PRIOR MARKUP VIEW] from the Status Variable Features Section of this document.

A Button that says "Grab Frame", that can be active only when the set of radio buttons above is set to "Live Fluoro Feed". When this button is pressed:
    The image Section changes from a video feed to a freeze frame of the image that is potentially going to be saved.
    A check is done on the status variable [CALIBRATE STATUS].
        If FALSE, then a pop-up can be displayed to the user.
            The label can be displayed: "To proceed with this image capture, a Grid calibration image can be captured as well, which has not occurred yet. Press "OK" to capture the calibration image right now. Press "Cancel" to cancel the current video capture action and lose the image data that is presently displayed"
            There can be an OK and cancel button.
            Pressing OK system can pull up the Calibrate Modal Window.
            Pressing Cancel system can: (1) close the pop-up, (2) resume the live video feed in the Image Section, and (3) return the user to the Capture Screen
        If TRUE the take no action
    An instance of the [CAPTURE DATA] dataset can be created, and the current live fluoro feed image gets saved as the image within that dataset
    The correction matrix can be accessed from the [CALIBRATE DATA] data structure, and then can be used to reseal the image to correct for distortion.

the radio button can be changed to "Current Capture" from "Live Fluoro Feed"

the "Grab Frame" images can become ghosted and inactive.

The right pane system can contain:

A Title at the top "STATUS: [Status Text]". [Status Text]=

"Capture and markup complete" In the case that [MARKUP STATUS]=Step 5 and [MARKUP SAVE SATUS]="Saved"

"Markup in process" In the case that [MARKUP STATUS]=Step 1 to Step 4

"Need to Save or Cancel Changes" In the case that [MARKUP STATUS]=Step 5 and [MARKUP SAVE SATUS]="Unsaved"

"Needs markup (capture complete)" In the case that [MARKUP STATUS]=Step 0

An Area for Directions, which is visible only when the [Status Text]="Needs markup (capture complete)." Or "markup in process"

A Text Box Labeled "Markup Directions" in which Direction text is displayed.

A Markup Diagram, which can assume one of five configurations

Figure 12:
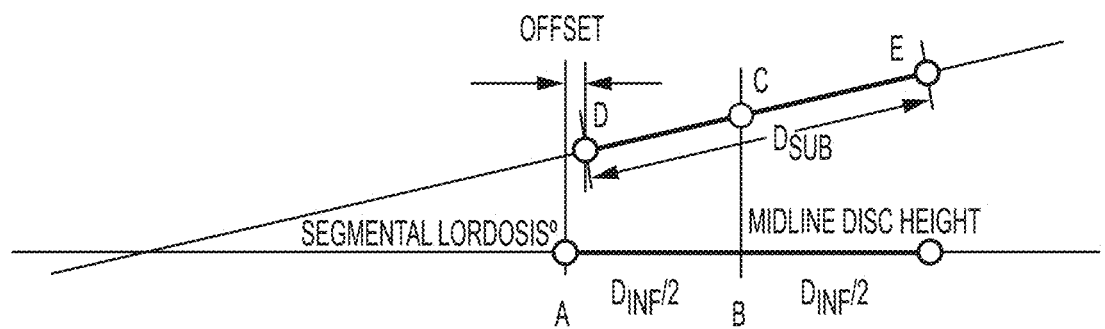
FIG. 12 illustrates an exemplar geometric transformation calculation.

For steps 1, 2, 4, and 5, the Markup Diagram assumes the form shown in FIG. 12 (green items are instructions, not part of the diagram). The red dot is placed at the appropriate corner (Step 1=POST/INF, Step 2=ANT/INF, Step 4=POST/SUP, Step 5=ANT/SUP)

In the boxes, the text label system can say "SUP." and "INF" if [MARKUP LEVEL] ="Unspecified". Otherwise, they say "LY" and "LX" respectively, where "LY" is the label of the superior vertebral body of the level and "LX" is the label of the inferior vertebral body of the level. See, FIG. 10.

For step 3, the Markup Diagram can be a row of 6 radio buttons, with labels: L1, L2, L3, L4, L5, S1.).

A set of buttons "Cancel" and "Save", which can be active whenever [MARKUP SAVE STATUS] is set to "Unsaved"

Upon Pressing "Save", the [MARKUP POINTS], [MARKUP LEVEL] can be saved and the [MARKUP SAVE STATUS] can be set to "SAVED"

Upon Pressing "Cancel", none of the changes that have been made to data since arriving at the "Capture" screen can be saved.

Upon pressing either, active control can be switched from Capture Screen back to Main Screen.

A Compare to Prior Spine Markup Area, which can be visible whenever the [MARKUP LEVEL] is not "Unspecified"

In the user configuration, a default value is assigned for default view for Compare to Prior Spine Markup. There can be a label "Compare to Prior Spine Markup", next to a drop down box that allows the user to change the value the variable [COMPARE PRIOR MARKUP VIEW]. See the Status Variable Features for more details about this variable.

The specified image can be accessed, and can be cropped to the Level specified by [MARKUP LEVEL] according to the cropping features provided in the "Main Screen, Left Pane: Disc Space View" Section of this document.

The cropped view can be displayed, with the four fiducials associated with the levels placed on top.

In the case that [MARKUP STATUS] is less than Step 3 or higher, the view can be displayed such that the view is rotated to align the Inferior edge of the disc space with the current capture.

Else, the view can be displayed in its native orientation.

In the case that the "VIEW:" radio buttons are set to "Current Capture" OR "Prior capture", AND the associated [MARKUP STATUS]=Step 0 through Step 4; then On the left pane the 7 tabs at the top, and on the right pane the other two tabs at the top ("Surgery Summary" and "Level Summary") system can all be ghosted/inactive The Image Section of the Capture screen system can:

Display fiducial markers on the images. Fiducial markers are objects placed in the field of view as a point of reference. The number and composition of the fiducials can be based on the [MARKUP STATUS] variable:

Step 1: 1_INF_VERT_POST_SUP_CORNER

Step 2: Add 2_INF_VERT_ANT_SUP_ CORNER, and create a line with that as an endpoint and the other one at 2_INF_VERT_ANT_SUP_CORNER Step 3: Add 3_SUP_VERT_POST_INF_CORNER Step 4: Add 4_SUP_VERT_ANT_INF_CORNER, and create a line with that as an endpoint and the other one at 3_SUP_VERT_POST_INF_CORNER Highlight a previously-placed fiducial as a user moves the mouse over it, allowing the following actions upon a click:

Enable the user to edit the location of the fiducials on the image by click/Dragging them. As they are click/dragged, if there is a line connecting a fiducial to another fiducial, the line length/angle changes as the other fiducial stays fixed Enable the user to edit the location of lines that connect the fiducials by click/dragging them. As they are click/dragged, the line and both endpoints move in lock step.

The user can be initiated into a workflow that progresses from a starting point defined by the current [MARKUP STATUS], and that terminates upon the user clicking "SAVE", or "CANCEL"

Step 0:

Configuration of the Area for Directions

Direction text:

If [MARKUP LEVEL] is set to a level (i.e. not "unspecified"): "Mark the posterior corner of [LX]". "LX"=the label of the inferior vertebral body of [MARKUP LEVEL]

If [MARKUP LEVEL] is "Unspecified": "Mark the Posterior corner of the inferior vertebral body"

Markup Diagram description: Red dot at POST/INF corner of disc space

Step 1: [MARKUP STATUS] system can increment from Step 0 to Step 1 when the user selects a point on the Image Section of the Capture Page.

[MARKUP POINT] can be saved (1_INF_VERT_POST_SUP_CORNER)

[MARKUP SAVE STATUS] can be set to "Unsaved"

A line can be created, with an endpoint at (1_INF_VERT_POST_SUP_CORNER) and with another endpoint at the current cursor location. As the user moves the mouse, the line changes in angle and length, and if the user moves mouse off the Image the line stops at the edge of the image but goes in a direction where the mouse is.

Configuration of the Area for Directions

Direction text:

If [MARKUP LEVEL] is set to a level (i.e. not "unspecified"): "Mark the anterior corner of [LX]". "LX"=the label of the inferior vertebral body of [MARKUP LEVEL]

If [MARKUP LEVEL] is "Unspecified": "Mark the anterior corner of the inferior vertebral body"

Markup Diagram description: Red dot at ANT/INF corner of disc space

Step 2-3: [MARKUP STATUS] system can increment from Step 1 to Step 2 when the user selects a point on the Image Section of the Capture Page.

[MARKUP POINT] can be saved (2_INF_VERT_ANT_SUP_CORNER)

A line can be placed, with endpoints at (1_INF_VERT_POST_SUP_CORNER) and (2_INF_VERT_ANT_SUP_CORNER).

The cursor system can resume normal functions.

[MARKUP SAVE STATUS] can be set to "Unsaved"

In the case that If [MARKUP LEVEL] is set to a level (i.e. not "unspecified"):

An additional step is added:

Direction text: "Label the inferior vertebral body"

Markup Diagram description: Display a row of 6 radio buttons, with labels: L1, L2, L3, L4, L5, S1.

Selecting a radio button here sets the [MARKUP LEVEL] to the appropriate level

The radio buttons at the top of the left pane of the Capture window, which are synchronized to the [MARKUP LEVEL] Variable, can be updated as appropriate.

Upon either selecting a radio button here associated with the inferior vertebral body of a level, or selecting a level from the radio buttons at the top of the left pane of the Capture window, the [MARKUP STATUS] system can increment from Step 2 to Step 3

Else ([MARKUP LEVEL] is NOT "Unspecified"), [MARKUP STATUS] System can increment from Step 2 to Step 3

Step 3: Configuration of the Area for Directions

Direction text: "Mark the posterior corner of [LY]". "LY"=the label of the superior vertebral body of [MARKUP LEVEL]

Markup Diagram description: Red dot at POST/SUP corner of disc space

Step 4: [MARKUP STATUS] system can increment from Step 3 to Step 4 when the user selects a point on the Image Section of the Capture Page.

[MARKUP POINT] can be saved (3_SUP_VERT_POST_INF_CORNE)

A line can be created, with an endpoint at (3_SUP_VERT_POST_INF_CORNE) and with another endpoint at the current cursor location. As the user moves the mouse, the line changes in angle and length, and if the user moves mouse off the Image the line stops at the edge of the image but goes in a direction where the mouse is.

[MARKUP SAVE STATUS] can be set to "Unsaved"

Configuration of the Area for Directions

Direction text: "Mark the anterior corner of [LY]". "LY"=the label of the superior vertebral body of [MARKUP LEVEL]

Markup Diagram description: Red dot at ANT/SUP corner of disc space

Step 5: [MARKUP STATUS] system can increment from Step 4 to Step 5 when the user selects a point on the Image Section of the Capture Page.

[MARKUP POINT] can be saved (4_SUP_VERT_ANT_INF_CORNER)

A line can be placed, with endpoints at (3_SUP_VERT_POST_INF_CORNER) and (4_SUP_VERT_ANT_INF_CORNER).

The cursor system can resume normal functions.

[MARKUP SAVE STATUS] can be set to "Unsaved"

Once the above actions have occurred, the user can either press "Save" or "Cancel" (or "Exit" or "Load Patient") to progress.

In the case that the "VIEW:" radio buttons are set to "Current Capture" OR "Prior capture" and the associated [MARKUP STATUS]=Step 5

The Image Section of the Capture screen system can:

Display fiducials on the images, The number and composition of which can be based on the [MARKUP STATUS] variable:

Step 1: 1_INF_VERT_POST_SUP_CORNER

Step 2: Add 2_INF_VERT_ANT_SUP_CORNER, and create a line with that as an endpoint and the other one at 2_INF_VERT_ANT_SUP_CORNER Step 3: Add 3_SUP_VERT_POST_INF_CORNER Step 4: Add 4_SUP_VERT_ANT_INF_CORNER, and create a line with that as an endpoint and the other one at 3_SUP_VERT_POST_INF_CORNER Highlight a previously-placed fiducial whenever a user moves the mouse over it, allowing the following actions upon a click:

Enable the user to edit the location of the fiducials on the image by click/Dragging them. As they are click/dragged, if there is a line connecting a fiducial to another fiducial, the line length/angle changes as the other fiducial stays fixed Enable the user to edit the location of lines that connect the fiducials by click/dragging them. As they are click/dragged, the line and both endpoints move in lock step.

Whenever any of the [MARKUP POINTS] are changed by the user making edits to the location of fiducials overlaid on the image, the [MARKUP SAVE STATUS] is set to "Unsaved"

In the case that [MARKUP SAVE STATUS] is set to "UNSAVED"
    On the left pane the 7 tabs at the top, and on the right pane the other two tabs at the top ("Surgery Summary" and "Level Summary") system can all be ghosted/inactive.
    The user can either press "Save" or "Cancel" (or "Exit" or "Load Patient") to progress.

Modal Windows (Accessible Via the Main Screen and Capture Screen)
    Modal windows can be accessible via the Main Screen and Capture Screen.
    There can be the following modal windows:
        Load New Patient
        Load Previous Session
        Edit Midline Disc Height (A1)
        Edit Offset (A2)
        Edit Lordosis (A3)
        Lordosis Distribution Calculations (Routhenfluh) (B1)
        Lordosis Distribution Calculations (Roussouly) (B2)
        Edit Correction for Anticipated Subsidence (C1)
        Calibrate (D)
    The modal windows, when accessed, can be the only active window, and the previous active window is greyed out, unless/until the user either takes an action within the window that closes it or the user clicks on a greyed out portion of the previous active window, both of which have the effect of closing the modal window.

Load New Patient
    There can be a title "Load a new patient to start a session"
    There can be a button "Re-Open Previous Session" which, when pressed, system can close the Load New Patient modal window and open the Load Previous Session modal window.
    There can be a means for the user to select a patient file for loading from a removable media
        The list of files to select from system can include FIRST NAME/LAST NAME initial and date of birth (DOB)
        List items can be sorted with newest first
        Pressing Select system can initiate a load of that patient file.
            The system can copy files
            The system can decrypt the files
            The system can initialize a user session based on the contents of the files
            The system can present a status window (See Load New Patient—SUBWINDOW2) to the user to inform the user of the status of the process of initializing the user session. This window system can also allow the user to cancel the load, which returns the user to the Load New Patient modal window
            Once loaded and initialized, the user can be returned to the Main Screen.
        If possible, the system can,
            prior to initiating a potentially lengthy load and initialization cycle, first read and decrypt the patient's full name, DOB, and study date,
            Present said data to the user in a pop-up (See Load New Patient SUBWINDOW1) wherein the user confirms or cancels the load operation.
        If user confirms the patient data, the:
            a check is done on the user type, and for OR ADMIN user types:
            a list of surgeons pops-up, and the OR Admin user selects the surgeon who is running the case from the list of all SURGEON users on the system.
            Once this gets set, a check is done to see if the Surgeon's user has ever been through the click-through agreement in the User Configuration pages.
            If so, no action.
            If not, the user is instructed to log off and have the surgeon user login and accept the configuration click through, and the patient is not loaded, active control goes back to the Load New Patient modal window.
            active control goes to the initialization status window if still loading/initializing, or active control goes to the Main Screen if initialization process is complete.
            If the user presses cancel, active control goes back to the Load New Patient modal window.
            The more lengthy full load and initialization operations can begin once the pop-up has been popped up (i.e. while the user is being presented with SUBWINDOW 1 and taking the time to react to it, the system in the background is completing the load/initialize operation).
    There can be a "Cancel" Button, which system can close the Load New Patient modal window and Return the user to the Screen from which the user came.

Load Previous Session
    There can be a title "Re-Open a Previous Session"
    There can be a means for the user to select a patient file for loading from a repository on the computers fixed media (hard drive) that contains previously stored user sessions.
        The list of files to select from system can include:
            First name, Last Name, DOB, Date of Study, Date of prior session
        List items can be sorted with newest first (with respect to the date of prior session)
        The list of files to select from is determined by:
            For SURGEON users, whether or not the site-level parameter is set that allows surgeons to view data from other surgeons at the same site.
            For ADMIN users, all patients at a given site.
        Pressing Select system can initiate a load of the specified session files.
            The system can initialize a user session based on the contents of the files such that it represented the last state of the user session data prior to the last exit action that closed it.
            The system can present a status window (See Load New Patient SUBWINDOW2) to the user to inform the user of the status of the process of initializing the user session. This window system can also allow the user to cancel the load, which returns the user to the Load Previous Session modal window
            Once loaded and initialized, the user can be returned to the Main Screen.
    There can be a "Cancel" Button, which system can close the Load Previous Session modal window and Return the user to the Screen from which the user came.

Edit Midline Disc Height (A1), Edit Offset (A2), Edit Lordosis (A3)
  Users can be able to access these pages in one of two ways:
    There is a minimum number of levels needed to calculate an average Disc Height, Offset, and Lordosis that is part of the User configuration. Whenever the user attempts to select a level for exclusion such that the total number of level not selected for fusion goes below this minimum, then this can be allowed, but this window can be popped up.
    If the user hits the "edit disc height", "edit offset", or "edit lordosis" buttons
  Edit Midline Disc Height (A1) and Edit Offset (A2) are nearly identical, and are described in the same section (with differences identified).
    There can be a title "Edit Midline Disc Height" or "Edit Offset".
    There can be instructions: "Adjust the [Midline Disc Height/Offset] by selecting/deselecting levels for exclusion, or by directly adjusting the value on the edit box below. The column on the right allows each level to be set separately."
    There can be a matrix of data and objects:
      There can be five rows, one for each level "L1/L2" through "L5/S1"
      There can be five columns"
        A first column with header label "Excluded?", and a column of checkboxes that are linked with the check boxes on the Surgery Summary Object (from the Main Screen)
        A second column with
          header label "MIDLINE DISC HEIGHT (from system)" in the case of Midline Disc Height (A1) window; header label "Offset (from the vertebral motion analysis)" in the case of Edit Offset (A2) window
          a column of millimeter values (#.#)
        A third column labeled "Data for Average Calculation" with the values from the previous column, excluding those that which are selected in the first column
        Underneath the third column, there can be an edit box with up/down increment buttons (#.# mm).
        The value can be defaulted to the computed average (after exclusions).
        Upon a user edit to the value in this edit box, all of the values in the edit boxes in the fifth column system can change to the new edited value.
        To the left of that edit box, there can be the label "Average After Exclusions".
        Underneath the edit box and label above, there can be another row of data
        There can be a label directly below the label "Average After Exclusions" that system can say "Computed value"
        There can be the average value from that column displayed (#.# mm), which is the average of the non-excluded values, directly below the edit box.
        A fourth column with header label "Level Selected for Fusion?", and a column of checkboxes that are linked with the check boxes on the Surgery Summary Object (from the Main Screen) and also in the tabs on the left side of the Main Page.
        A fifth columns column with:
          header label "MIDLINE DISC HEIGHT" for Midline Disc Height (A1) window; header label "Offset" for Edit Offset (A2) window
          For those levels that are selected for fusion, a column of edit boxes with up/down increment buttons.
          Each of the edit boxes can be independently editable, and when users make edits to any of these edit boxes, it has no effect on the value of the edit box underneath the third column
    There can be a "Restore Default" Button that can be visible whenever the value of the Disc Height or Offset status variable [CHECKBOX COLUMNS ACTIVE] is FALSE.
      Clicking the restore default values will set all values back to the computed average value (after exclusions), and set the [CHECKBOX COLUMNS ACTIVE] to true.
    There can be Save button, which system can save the changes made since the modal window has been active, then close the window and return control to the referring page.
    There can be Cancel button, which system can close the window and return control to the referring page.
    In the case that the current number of non-excluded levels is below the minimum value specified in the User Config:
      Alert text system can appear, underneath the first column "Too many levels are excluded. Your minimum is at least X non-excluded levels. You can deselect a level to proceed."
      The Save button can be ghosted and inactive
      If the user clicks "Cancel", then all of the edits made since the modal window was popped up get undone.
      In the case that the modal window had been popped up by the user's selection of a level for exclusion that resulted in the total number of non-excluded levels to go below the minimum value set in user config, the level that had been selected for exclusion to prompt the pop-up of the modal window is deselected.
  Edit Lordosis (A3) is described below:
    There can be a title "Edit Target Segmental Lordosis".
    There can be instructions: "The target segmental lordosis calculations are Shown Below. The model can be adjusted by adjusting the levels excluded from the lordosis model."
    There can be a matrix of data and objects:
      There can be five rows, one for each level "L1/L2" through "L5/S1"
      There can be four columns on the left have of the window
        A first column with header label "Excluded?", and a column of checkboxes that are linked with the check boxes on the Surgery Summary Object (from the Main Screen)
        A second column with header label "A. Segmental Lordosis (From vertebral motion analysis)" plus a column of degree values)(#°

A third column with header label "B. DISTRIBUTION (from Config)" plus a column of percent values (#%). There can be a A fourth column labeled "QUOTIENT: % PER DEGREE (Calc, AB)" with the values from the previous column, excluding those that are selected in the first column.

Underneath the fourth column, is the average of the column (#.#) after exclusions, with a label to the left that says "C. Average=".

Above the four columns is a label "Step 1: Determine average degrees per percent contribution to lordosis for non-excluded levels"

There can be three columns on the right half of the window, such that the rows continue to align from the matrix of data.

A first column with header label "Level Selected for Fusion?", and a column of checkboxes that are linked with the check boxes on the Surgery Summary Object (from the Main Screen) and also in the tabs on the left side of the Main Page.

A second column with header label "D. TARGET LORDOSIS (calc, B*C)" and a column of degree values (#°), which system can only contain values for those rows with a check in the checkbox in the "Level Selected for Fusion?" column of checkboxes.

A third column with header label "CHANGE FROM VERIEBRAL MOTION ANALYSIS (calc, D-A)" plus, for those levels that are selected for fusion, a column of degree change values (+#° or −#°).

Underneath the third column is the sum of the column above given as a degree change value (+#° or −#°), with a label to the left that says "Sum="

Above the three columns is a label "Step 2: For all levels selected for fusion, project target lordosis based on an adjusted distribution function."

There can be Save button, which system can save the changes made since the modal window has been active, then close the window and return control to the referring page There can be Cancel button, which system can close the window and return control to the referring page.

In the case that the current number of non-excluded levels is below the minimum value specified in the User Config:

Alert text system can appear, underneath the first column "Too many levels are excluded. Your minimum is at least X non-excluded levels. You can deselect a level to proceed."

The Save button can be ghosted and inactive

If the user clicks "Cancel", then all of the edits made since the modal window was popped up get undone.

In the case that the modal window had been popped up by the user's selection of a level for exclusion that resulted in the total number of non-excluded levels to go below the minimum value set in user config., the level that had been selected for exclusion to prompt the pop-up of the modal window is deselected.

Lordosis Distribution Calculations (Routhenfluh) (B1)

There can be a title "Calculations: Allocating additional lordosis across levels".

There can be instructions: "The total additional lordosis, as well as the additional segmental lordosis by level, can be directly adjusted."

There can be a matrix of data and objects:

There can be five rows, one for each level "L1/L2" through "L5/S1"

There can be four columns

A first column with header label "Level Selected for Fusion?", and a column of checkboxes that are linked with the check boxes on the Surgery Summary Object (from the Main Screen) and also in the tabs on the left side of the Main Page.

A second column with header label "DISTRIBUTION (from Config)" plus a column of percent values (#%). Underneath this column there is a label "Σ≈100%" (note curvy equal sign).

A Third column with header label "A. DISTRIBUTION (Adjusted)" plus a column of percent values (#%), excluding values from rows that are not selected for fusion, and normalized such that the sum of all non-excluded levels can be 100%. Underneath this column there is a label "Σ=100%" (note normal equal sign), and under that label another label "The distribution function is adjusted so that the sum of levels selected for fusion is 100%."

A Fourth column with header label "ADDITIONAL SEGMENTAL LORDOSIS (calc, A*B)" plus two sub-columns, with each sub-column only containing data for those levels that are selected for fusion:

the first with sub-column header label "Computed value" and a column of degree change values (+#° and −#°)

the second with sub-column header label "User-Edited Value" a column of Edit boxes with up/down increment buttons, defaulted to the computed value, and containing degree change values (+#° and −#°).

Changing the value of any of these edit boxes system can change the value of the edit box underneath the fourth column, second sub-column Underneath the Fourth column:

There can be a degree change value (+#° and −#°) under the first sub-column of the fourth column that represents the sum of the values displayed in the columns above (which system cannot include the excluded levels).

To the left of that value there can be a label "B. ADDITIONAL LORDOSIS"

There can be an Edit box with up/down increment buttons, defaulted to the computed value, and containing degree change values (+#° and −#°) under the second sub-column of the fourth column Any change to the value of this edit box system can:

Change the values of the edit boxes in the fourth column, second sub-column.

Change the "Additional Lordosis" value that is presented on the Surgery Summary object, and vice versa.

There can be Save button, which system can save the changes made since the modal window has been active, then close the window and return control to the referring page There can be Cancel button, which system can undo all of edits made since the modal window was popped up, then close the window and return control to the referring page Lordosis Distribution Calculations (Roussouly) (B2)

There can be a title "Calculations: Allocating additional lordosis across levels".

There can be instructions: "The total additional lordosis for each of the upper and lower arcs, as well as the additional segmental lordosis by level, can be directly adjusted."

There can be a matrix of data and objects:

There can be five rows, one for each level "L1/L2" through "L5/S1"

There can be five columns

A first column with header label "Level Selected for Fusion?", and a column of checkboxes that are linked with the check boxes on the Surgery Summary Object (from the Main Screen) and also in the tabs on the left side of the Main Page.

A second column with header label "DISTRIBUTION (from Config)" plus a column of percent values (#%). Around the column of data is a box with the label "Σ≈100%" (note curvy equal sign)

A third, fourth, and fifth columns, which all get split horizontally based on the location of the APEX of the lumbar curve (See Calculations Features section for more detail about the Apex calculation).

A Third column:

header label "A. DISTRIBUTION (Adjusted)"

a column of percent values (#%), excluding values from rows that are not selected for fusion.

Around each group of values (above and below the horizontal split), there is a box with the label "E=100%" (note normal equal sign)

Underneath the column is another label "The distribution function is adjusted so that the sum of levels selected for fusion within each of the upper and lower arcs is 100%."

A Fourth column:

header label "B. ADDITIONAL LORDOSIS (input by user)"

In the vertical center of each section (above and below the horizontal split), an edit box with up/down increment button. In the upper area, the label above the edit box is "Upper Arc". In the lower area, the label above the edit box is "Lower Arc".

Any changes to the value in either of the edit boxes in this column system can:

change the value in the corresponding edit boxes in the fifth column (second sub-column).

change the value of the corresponding edit box (either Upper Arc or Lower Arc) on the Surgery Summary Object.

A Fifth column:

header label "ADDITIONAL SEGMENTAL LORDOSIS (calc, B*C)"

plus two sub-columns, with each sub-column only containing data for those levels that are selected for fusion:

the first with sub-column header label "Computed value" and a column of degree change values (+#° and −#°)

the second with sub-column header label "User-Edited Value" a column of Edit boxes with up/down increment buttons, defaulted to the computed value, and containing degree change values (+#° and −#°).

Changing the value in any of the edit boxes in this column system can change the value in the corresponding edit box(es) in the fourth column.

There can be Save button, which system can save the changes made since the modal window has been active, then close the window and return control to the referring page There can be Cancel button, which system can undo all of edits made since the modal window was popped up, then close the window and return control to the referring page Edit Correction for Anticipated Subsidence (C1)

There can be a title "Edit Correction for Anticipated Subsidence".

There can be instructions: "The correction for anticipated subsidence is a geometric calculation of the anticipated lordosis loss that would occur given a specific amount of millimeter lordosis and assumed implant length*. Change either of these two parameters to alter the angle of require correction to offset this subsidence, or vice versa."

There can be a matrix of data and objects:

There can be five rows, one for each level "L1/L2" through "L5/S1"

There can be six columns:

A first column with header label "Level Selected for Fusion?", and a column of checkboxes that are linked with the check boxes on the Surgery Summary Object (from the Main Screen) and also in the tabs on the left side of the Main Page.

A second column with header label "A. LENGTH OF SUPERIOR EDGE OF INFERIOR VERTEBRAL BODY (from vertebral motion analysis)" plus a column of millimeter values (#.# mm), excluding values from rows that are not selected for fusion.

A third column:

header label "B. ASSUMED LENGTH OF IMPLANT"

plus two sub-columns, with each sub-column only containing data for those levels that are selected for fusion:

the first with sub-column header label "From User Config" and a column of millimeter values (# mm)

the second with sub-column header label "User-Edited Value" a column of Edit boxes with up/down increment buttons, defaulted to the value from User Config, and containing millimeter values (# mm).

A fourth column with header label "C. OFFSET (from vertebral motion analysis)" plus a column of millimeter values (#.# mm), excluding values from rows that are not selected for fusion.

A fifth column:
- header label "D. MAXIMUM ANTICIPATED ANTERIOR SUBSIDENCE*"
- plus two sub-columns, with each sub-column only containing data for those levels that are selected for fusion:
  - the first with sub-column header label "computed value" and a column of millimeter values (#.# mm)
  - the second with sub-column header label "User-Edited Value" a column of Edit boxes with up/down increment buttons, defaulted to the value from User Config, and containing millimeter values (#.# mm).

A sixth column
- with header label "E. CORRECTION FOR ANTICIPATED SUB SIDENCE**"
- plus two sub-columns, with each sub-column only containing data for those levels that are selected for fusion:
  - the first sub-column header label "computed value" contains a column of degree change values (+#° and –#°)
  - the second sub-column header label "User-Edited value" Edit boxes with up/down increment buttons, containing degree change values (+#° and –#°), defaulted to the computed value.
- Underneath the sixth column are two values, one for each sub-column, which is the sum of the sub-column, in degree change values (+#° and –#°), and with the label "Sum=" to the left.

There can be a label on the bottom of the frame for notes:
"* This estimate of potential lordosis loss due to subsidence is a geometric calculation based on the individual vertebral body dimensions of each patient. This calculation uses an assumed "Maximum Anticipated Anterior Subsidence" which represents the upper end of expected subsidence. Consider adjusting upward from the default value when patient has poor bone quality or when interbody device placement is posterior. Consider adjusting downward from the default if the level receives anterior fixation or when interbody device placement is anterior.

θ=ArcTangent (Length/*D*); Length=*A/2+B/2–C"*   **Formula for E:

There can be Save button, which system can save the changes made since the modal window has been active, then close the window and return control to the referring page There can be Cancel button, which system can undo all of edits made since the modal window was popped up, then close the window and return control to the referring page Calibrate (D)
- There can be the title "Collect Grid Calibration Image:
- There can be instructions: "The C-arm can be calibrated. Please capture an image of the grid. For more information about how to properly capture the grid image, please press help.
- Below is an image that is coming from the fluoroscope. Please capture a grid image on the fluoroscope, and when a grid image appears below press "Accept Image" to continue."
- There can be a help button that pulls up a help screen
- There can be a space for the fluoro image feed that can be the native size of the image. (optimized for 1 k×1 k pixels, but able to accept up to 2 k×1.5 k)
- There can be an "Accept Image" button, that when pressed system can:
  - grab the current image, and save it to the [CALIBRATE DATA] data structure
  - derive a correction matrix from the saved calibration image, and save this to the [CALIBRATE DATA] data structure.
  - Change the status variable [CALIBRA FED YET] to TRUE
  - Close the window and return the user to the referring page.
    - In the case that the user came to the Calibrate (D) modal window after having pressed "Grab Frame" then "OK" on the Capture Screen, then the user system can return to the Capture Screen, and resume the set of actions specified to occur directly following the check that is done on the status variable [CALIBRATE STATUS] that occurs after the user presses "Grab Frame".
- There can be a "Cancel" button, that when pressed does one of two things:
  - If the user came to the Calibrate (D) modal window after having pressed "Grab Frame" then "OK" on the Capture Screen, then:
    - a message pop-up will be displayed "Cancelling the calibration will make it impossible to continue with the prior video capture action, and the image that was captured will be lost. Press "CANCEL & LOSE PRIOR CAPTURE" or "GO BACK TO FINISH CALIBRATION"".
    - If user selects "Cancel", then: (1) the message pop-up and the Calibrate modal window can be closed, (2) return active control to the Capture screen, which itself will have a pop-up message open, which system can close, and (3) on the Capture screen the live video feed system can resume in the Image Section.
    - If user selects "Go back", then the message window system can close and active control system can revert back to the Calibrate modal window.
  - ELSE, close the window and return the user to the referring page.

Configure Screens
The Configure Screen system can have visible and active a "Save" and a "Cancel Button".
The same upper frame and buttons from the upper right section of the Main Screen (with the Exit and Load Patient button) system can be active and visible on the Configure Screen.
Upon pressing "Save", a pop-up click-through agreement is served to the user:
  The agreement system can present the text:
    "All of the preceding user configurations represent my personal medical judgment. The convenience features included in this software do not represent a specific medical diagnosis and it is my responsibility to determine their clinical significance, if any, based my training, experience and relevant clinical circumstances. I further understand and acknowledge that the vertebral motion analysis can be based on automatically or semi-automatically generated data, and that I can manually review all potentially clinically relevant information before relying upon any data presented via the system for clinical decision making I understand that the Company will be storing my user configuration data, and will treat this information as confidential and secure it to the same extent it secures protected patient health information. I have read and understand the above."

The user can be presented with buttons "I Agree" or "Cancel"

Pressing "Cancel" system can revert active control back to the Config Screens.

Pressing "I Agree" system can:

Update the data associated with the surgeon user to note that the click-through agreement has been executed (see the section "Functional Features: Data saving and storage").

Close the pop-up

Revert active control back to the page the user was on prior to pressing the "Configure" button.

There can be four tabs on the Configure Screen

There can be a first tab labeled "OPTIONS"

There can be a section labeled "Default Image Viewing Options"

There can be a sub-section labeled "OVERLAYS".

There can be a column of 5 items, each item comprised of a checkbox (all defaulted to on), icon, and label, and said item labels being "Target Construct", "Current Capture", "Reference View", "Mobility Range", "Gravity (plumb)"

There can be a sub-section labeled "DISPLAY OPTIONS".

There can be a checkbox labeled "Images" (defaulted to on)

Indented from the "Images" label, there can be a set of three radio buttons labeled "Reference View", "Target Construct", and "Current Capture". Default value is "Current Capture"

There can be a checkbox labeled "Labels" (defaulted to on)

There can be a sub-section labeled "ORIENTATION".

There can be a set of three radio buttons labeled "Reference View", "Current Capture", "Native", and "Gravity". Default value is "Gravity"

Next to the "Gravity" label, and visible when the "Gravity" radio button is selected, is a drop box labeled "If unavailable, use", that allows the user to select from a list of "Current Capture" and "Native", which comes defaulted to "Native"

There can be a sub-section labeled "LINEAR MEASUREMENTS".

There can be a set of three radio buttons labeled "% Max. Range", "Millimeters", and "% Vertebral Body Depth". Default value is "Millimeters"

There can be a sub-section labeled "DEFAULT REFERENCE VIEW".

There can be two sub-areas, connected by a selector object that allows the user to select between the two sub-areas (defaulted to select the first sub-area The first sub-area can be labeled "MIN/MAX VIEWS", and can have two sets of radio buttons. The first set can have two radio buttons labeled "MM." and "Max." (Defaulted to Max.). The second set can have four radio buttons labeled "Lordosis", "Reduction", "Anterior Disc Height", "Posterior Disc Height" (defaulted to Lordosis).

The second sub-area can be labeled "SPECIFIC VIEWS", and can have two sets of radio buttons. The first set can have five radio buttons labeled "Standing, NO device, bending views", "Standing, WITH device, bending views", "Side-lying, bending views", "Supine, neutral view" and "Prone, neutral view" (defaulted to "Standing, NO device, bending views".). The second set can have three radio buttons labeled "Neutral", "Flexion", and "Extension" (defaulted to neutral).

This second set of three radio buttons can be ghosted/inactive if the first set of radio buttons assumes either of the values "Supine, neutral view" and "Prone, neutral view"

There can be a sub-section labeled "Default Comparison View (during Capture)".

There can be two sub-areas, connected by a selector object that allows the user to select between the two sub-areas (defaulted to select the second sub-area)

The first sub-area can be labeled "MIN/MAX VIEWS", and can have two sets of radio buttons. The first set can have two radio buttons labeled "MM." and "Max." (Defaulted to Max.). The second set can have four radio buttons labeled "Lordosis", "Reduction", "Anterior Disc Height", and "Posterior Disc Height" (defaulted to Reduction).

The second sub-area can be labeled "SPECIFIC VIEWS", and can have two sets of radio buttons. The first set can have five radio buttons labeled "Standing, NO device, bending views", "Standing, WITH device, bending views", "Side-lying, bending views", "Supine, neutral view" and "Prone, neutral view" (defaulted to "Supine, neutral view".). The second set can have three radio buttons labeled "Neutral", "Flexion", and "Extension" (defaulted to neutral).

This second set of three radio buttons can be ghosted/inactive if the first set of radio buttons assumes either of the values "Supine, neutral view" and "Prone, neutral view"

There can be a checkbox labeled "Same as Default Reference View" which, when selected, will copy the selections in the Default Reference View into this section.

There can be a second tab labeled "TARGET CONSTRUCT"

There can be a section labeled "Assumptions for Determining Sagittal Alignment Corrections", which can be split into two sub-sections There can be a set of two radio buttons, each one located at the top of each subsection, labeled "Rothenfluh, 2014" and "Roussouly, 2005).

Next to each radio button label, there is an icon "i" which system can bring up an image labeled either [ROTHENFLUH IMAGE] or [ROUSSOULY IMAGE].

Underneath the "Rothenfluh, 2014" radio button:

There can be an edit box with up/down increment buttons, labeled "Target Post-Op PI-LL:", value in degrees (#°), defaulted to 10 degrees.

There can be a label "Default constructs include PI-LL correction (if PI-LL is less than target)?" Underneath the label can be a set of two radio buttons, labeled "Include Correction in Default" and "Default does NOT include Correction" (defaulted to Corrected)

Underneath the "Roussouly, 2005" radio button, there can be the label "Roussouly method involves manually inputting the target angles for the upper and lower lumbar arcs."

There can be a section labeled "Assumptions for Distributing Segmental Lordosis. Select a Lordosis Distribution Function. This is simply a set of five percent values, which sum to approximately 100%. This represents the segmental lordosis at each level as a % of total lumbar lordosis."

Underneath the label there can be a 5×4 matrix of data:
A set of five columns header labels "L1/L2" "L5/S1"
A set of four radio buttons with labels: "Panjabi, et. al. (1992)", "Stagnara, et. al. (1998)", "Average", and "User-defined". The radio button labels serve as row header labels. The default value is "Average"
There can be an "i" icon to the right of the "Average" label that system can bring up an image labeled [DISTRIBUTION FUNCTIONS IMAGE].
The first three rows can have the values displayed in FIG. 11:
The last row can be a set of user editable text boxes, defaulted to null, which allows a user to input a value between 1 and 100. Editing any of these boxes changes the radio button to be equal to "User-Defined".
Whenever data is entered and then saved, a normalized distribution function can be calculated and used whenever the distribution function data is used by the software, which can be normalized such that the sum of the five user-entered values can be equal to 100%.

There can be a section labeled "Calculation Assumptions"
There can be three edit boxes with up/down increment buttons, each defaulted to 2 and capable of assuming the values 1-4.
The labels on these edit boxes can be "Minimum number of non-excluded levels for the "Lordosis" calculation", "Minimum number of non-excluded levels for the "Disc Height" calculation", and "Minimum number of non-excluded levels for the "Offset" calculation"

There can be a third tab labeled "SUBSIDENCE"
There can be a section labeled "Default", which can have:
A checkbox labeled "Include additional lordosis to offset potential subsidence-related lordosis loss?*", defaulted to on.
An edit box with up/down increment buttons, displaying a value in millimeters (#.# mm), defaulted to 2.0 millimeters There can be a section labeled "MASS* Adjustment Assumptions"
A checkbox labeled "Adjust the MASS* value when gravity and the level are close to parallel?", defaulted to on.

An label, edit box with up/down increment buttons, second label, a second edit box with up/down increment buttons, and a third label
First edit box: label to the left of the edit box "Reduce MAAS* by", value is millimeters (#.# mm), defaulted to −1.0 mm.
Second edit box: label "when gravity and the level are within", value is in degrees)(##°, defaulted to 30 degrees
The third label: "degrees of being parallel (in standing, NO device, neutral view)."

There can be a section labeled "Assumed Implant Dimensions (for the geometric calculations)"
There can be two scales of 10 to 50 millimeters, on which users can specify whole number points (i.e. the sliders "snap" to the whole numbers).
The first scale can be labeled "VERTEBRAL BODY SIZE DEFINITIONS (anterior-posterior depth in millimeters)"
This scale can have two points defined by the user, corresponding to three contiguous regions labeled "Small", "Medium" and "large".
The default values can be: Small-Medium: 30 mm; Medium-Large: 35 mm.
The second scale can be labeled "ASSUMED RANGE OF INTERBODY DEVICE SIZE (anterior-posterior depth in millimeters)"
This scale can have six points defined by the user, corresponding to three ranges labeled "Small", "Medium" and "large", with each range comprising two points (start, end), which may or may not overlap or be contiguous.
The default values are:

| Range of Interbody Device A/P Depth | |
|---|---|
| Start | End |
| 14 mm | 22 mm |
| 18 mm | 26 mm |
| 22 mm | 30 mm |

There can be the footnote: "*This estimate of potential lordosis loss due to subsidence is a geometric calculation based on the individual vertebral body dimensions of each patient. This calculation uses an assumed "Maximum Anticipated Anterior Subsidence" which represents the upper end of expected subsidence. Consider adjusting upward from the default value when patient has poor bone quality or when interbody device placement is posterior. Consider adjusting downward from the default if the level receives anterior fixation or when interbody device placement is anterior."

There can be a fourth tab labeled "ALERTS"
There can be a section labeled "Surgical Considerations", which can have a 3×4 matrix of data and objects:
The first row can have the following three elements: an "Alert text" label, a second item comprised of a yellow triangle alert icon plus an edit box defaulted to the value "Possible", and a third element comprised of a red triangle alert icon plus an edit box defaulted to the value "Likely"
Rows 2-4 in the first column system can contain edit boxes defaulted to the values "Smith Peterson osteotomy", "Pedicle subtraction osteotomy (PSO)", and "ALL release procedure"

Cell (2,2) can have "Target PDH<X % PDH @ standing neutral", where X is an edit box (#%) defaulted to 100%.

Cell (2,3) can have "Target PDH<X % minimum PDH across all images", where X is an edit box (#%) defaulted to 100%.

Cell (2,4) can have "Target ADH>X % maximum ADH across all images", where X is an edit box (#%) defaulted to 125%.

Cell (3,2) can have "Target PDH<X % minimum PDH across all images", where X is an edit box (#%) defaulted to 100%.

Cell (3,3) can have "Target PDH is less than X", where X is an edit box (# mm) defaulted to 0 mm Cell (3,4) can have "Target ADH>X % maximum ADH across all images", where X is an edit box (#%) defaulted to 150%.

There can be a section labeled "Sagittal Alignment Alert Thresholds", which can have a 2×2 matrix of data and objects:

The 2 row labels can be "Rothenfluh" and "Roussouly"

There can be no column header labels.

Cell (1,1) can have a yellow triangle alert icon, and an edit box with up/down increment buttons, label "PI-LL>", value is in degrees)(##°, defaulted to 8 degrees Cell (2,1) can have a red triangle alert icon, and an edit box with up/down increment buttons, label "PI-LL>", value is in degrees)(##°, defaulted to 10 degrees Cell (2,1) can have two sub-sections, connected by a drop-down box that can select from the list of "AND" and "OR" (defaulted to "OR")

The first sub-section can be a set of four checkboxes, with labels "Type 1", "Type 2", "Type 3", and "Type 4". Defaulted to Type 1 and Type 2 being on.

The second sub-sections system can consist of an edit box with up/down increment buttons with a label on top, which is on top of a second edit box with up/down increment buttons with a label on top, which is on top of a third label:

First edit box: label "Pelvic Tilt between", value is degree (#°), defaulted to −25 degrees.

Second edit box: label "and", value is degree (#°), defaulted to 30 degrees.

The third label: "inclusive"

Cell (2,2) can have two sub-sections, connected by a drop-down box that can select from the list of "AND" and "OR" (defaulted to "AND")

The first sub-section can be a set of four checkboxes, with labels "Type 1", "Type 2", "Type 3", and "Type 4". Defaulted to Type 1 and Type 2 being on.

The second sub-sections system can consist of an edit box with up/down increment buttons with a label on top, value is degree (#°), defaulted to 30 degrees.

Status Variable Features

There can be a Boolean status variable [CALIBRATED YET]

The default value is FALSE

The value changes to TRUE the user pressing the "Accept Image" button on the Calibrate (D) modal window and the function to derive the correction matrix executes successfully.

There can be a status variable [CAPTURE STATUS] that is associated with each level.

The possible values can be: "No Capture Yet" or "Current Capture with no prior captures" or "Current Capture with Prior captures"

The default value can be "No Capture Yet"

The value of [CAPTURE STATUS] can be determined by the set of instances of [CAPTURE DATA]. For all instances, count the number of instances for which [MARKUP STATUS]=Step 5 and [MARKUP SAVE STATUS]="Saved":

"No Capture Yet" whenever the count is zero

"Current Capture with no prior captures" whenever the count is 1

"Current Capture with Prior captures" whenever the count is 2 or greater.

There can be a status Variable [MARKUP STATUS], [MARKUP LEVEL], and [MARKUP SAVE STATUS] associated with Capture Image These variables can be able to assume the values:

[MARKUP STATUS]: Step 0 to Step 5

[MARKUP LEVEL]: "Unspecified", "L1/L2" . . . "L5/S1"

[MARKUP SAVE STATUS]: "Saved" or "Unsaved"

These variables system can get initiated each time the user presses "Grab Frame" on the Capture Screen, (which triggers the creation a new instance of the [CAPTURE IMAGE] dataset).

[MARKUP STATUS] is set to Step 0

[MARKUP LEVEL] is set according to which radio button is selected. If no radio button is selected (i.e. [ACTIVE LEVEL]=Null), then this is defaulted to the value "Unspecified"

[MARKUP SAVE STATUS] is set to "Unsaved"

The [MARKUP LEVEL] Variable can be changed by the user at any time by interacting with the radio buttons at the top of the left pane of the Capture Screen.

The [MARKUP LEVEL], [MARKUP LEVEL], and [MARKUP SAVE STATUS] variable can also be changed according to the workflow described in the Capture Screen section of this document.

There can be the status variable [ADDITIONAL LORDOSIS FOR SA CORRECTION STATUS] that is associated with each user session.

The possible values can be: null, "Not Confirmed" or "Confirmed"

The default value can be:

If user config specifies Rothenfluh AND if user config specifies that PI-LL corrections ARE to be included in the default, then the default value can be "Not Confirmed".

Else, then the default value can be null

If user config specified Roussouly, then the default value can be null

The value of [ADDITIONAL LORDOSIS FOR SA CORRECTION STATUS] can be changed by any one of the two actions below, and once it changes its value from the default it typically does not revert to any other value On the Surgery Summary Object: (1) clicking on the "OK" on the button next to the Additional Lordosis edit box, (2) editing a value into this edit box, or (3) using the plus or minus increment buttons.

On the Lordosis Distribution Calculations, Rothenfluh (B1) modal window, pressing the "Save Button" (regardless of whether or not any values had been edited while the modal window had been active)

There can be a Boolean status variable [CHECKBOX COLUMNS ACTIVE] associated with each of the columns of checkboxes for excluding Disc Height and Offset.
  The default value can be TRUE
  The value of [CHECKBOX COLUMNS ACTIVE] changes to FALSE whenever, on the Edit Midline Disc Height (A1) or Edit Offset (A2) modal window, any of the values in the rightmost column differ from the computed average (after exclusions)
There can be a status Variable [ACTIVE LEVEL] associated with each patient use sessions
  The possible values can be: null, "L1/L2" "L5/S1"
  The default value can be null
  The value of [ACTIVE LEVEL] can be changed by any one of the three actions:
    The user clicking one of the five tabs ("L1/L2" "L5/S1") from within the set of seven tabs that is present on the upper portion of the left pane of both the Main Screen and capture Screen. When this occurs, ACTIVE LEVEL is set to the level that the user clicks.
    The user selecting a level in the upper portion of the left pane of the Capture Screen.
    The user completing a four point markup of a level's disc space while on the Capture Screen. When this occurs, ACTIVE LEVEL is set to the level that underwent the 4 point markup.
There can be status Variables [REFERENCE VIEW] and [COMPARE PRIOR MARKUP VIEW] associated with each patient use sessions
  These Variables comes defaulted to the view specified in the User Config pages.
  These variables are changeable wherever there is: (1) a drop down labeled "reference View" for [REFERENCE VIEW], or (2) a drop down labeled "Compare to Prior Spine Markup" for [COMPARE PRIOR MARKUP VIEW]
  Each of the [REFERENCE VIEW] items below may or may not have gravity data, however the Standing NO Device, neutral view can have gravity data
  These variables can assume the following values (also note the values below are the [VIEW TEXT] text string which appears in labels in some other sections of the software)
    Min/Max Views (there is an image for this)
      Max Lordosis
      Max Reduction
      Max ADH
      Max PDH
      Min Lordosis
      Min Reduction
      Min ADH
      Min PDH
    Specific Views (These only display if they exist):
      Standing NO Device Neutral
      Standing NO Device Flexion
      Standing NO Device Extension
      Supine
      Prone
      Standing WITH Device Neutral
      Standing WITH Device Flexion
      Standing WITH Device Extension
      Lying WITH Device Neutral
      Lying WITH Device Flexion
      Lying WITH Device Extension
    Prior Capture (this section of the list is only active if [CAPTURE STATUS] is set to "Current Capture with Prior captures"
      There can be a list of all previous prior, with each prior capture labeled as "X capture(s) ago ([time/date stamp]), ['markup complete" or "markup not complete"]".
        If [CAPTURE STATUS] "No Capture Yet", then the text above system can include the element "markup not complete", else this can be "markup complete".
      Each element on the list of Previous captures can be visible, if the prior captures has [MARKUP STATUS] of Step 5 and [MARKUP SAVE STATUS] of "Saved"
Data Structure Features:
An array of computed values based on default values, which system can get updated upon any change to the user config variables and change to the levels selected for fusion, but otherwise do not change throughout a testing session
  Additional Sagittal Alignment correction, by level (segmental) and across all level selected for fusion s
  Correction for Anticipated Subsidence, by level and across all levels selected for fusion
  Maximum Anticipated Anterior Subsidence (MAAS), by level.
  Target Construct default values, by level and across all levels selected for fusion
  Total Segmental lordosis for all levels selected for fusion (adding all of the above three items)
An array of current values, as edited by the user:
  via direct edit on an edit box
    Sagittal Alignment correction, by level and across all level selected for fusion s
    Correction for Anticipated Subsidence, Maximum Anticipated Anterior Subsidence, Assumed Implant Length, by level
    Total Segmental lordosis (adding all of the above three items)
    Midline Disc Height and Offset.
  via grab/drag or drag/rotate actions in the Disc Space Diagram.
    Target Construct values (lordosis, Midline disc height, offset)
  via selections/deselections from checkbox arrays
    Levels selected for fusion
    Levels selected for exclusions for lordosis, disc height, and offset
  Via an array of dropdowns:
    Lordosis data source by level
An array of current calculated values, based on the array of current user-set values, which system can include all of the variables specified to be calculated in the "Calculation Features" section. Note these are the values that get calculated based off the combination of default values and current values (as edited by the user).
There can be a data structure [CALIBRATE DATA] which can be created/updated upon a calibrate action (see Calibrate modal window), and which system can store an instance of an image and a correction matrix associated with the calibration action.

There can be a data structure [CAPTURE DATA], which can be created upon a video capture action that occurs in the Capture Screen
  Current Capture Image—This system can contain the image file that is created with the video capture action
  [MARKUP STATUS]—This can be a status variable (See Status Variable Features Section). This can assume the values Step 0 through Step 5
  [MARKUP LEVEL]—This can be a status variable (See Status Variable Features Section). This can assume the values "Unspecified", "L1/L2" "L5/S1".
  [MARKUP POINTS]—This is 4 coordinate (x,y) sets representing pixel locations relative to the Current Capture Image. The 4 coordinate sets are named:
    1_INF_VERT_POST_SUP_CORNER,
    2_INF_VERT_ANT_SUP_CORNER,
    3_SUP_VERT_POST_INF_CORNER,
    4_SUP_VERT_ANT_INF_CORNER
  [MARKUP SAVE STATUS]—This can be a status variable (See Status Variable Features Section). This can assume the values "Saved" and "Unsaved".
Alerts Features:
Alerts can have the following attributes: Severity (null, yellow, red), Short text (2 or 3 upper case letters), and a long text (a constructed text string).
There can be two types of alerts (Surgical Considerations and Sagittal Alignment alerts), each having its own set of icon/short text items as well as long text items
  Surgical consideration alerts (PSO, SP, ALL)
    These alerts can be structured as a posterior alert and an anterior alert, each of which can be activated or deactivated independently.
    The icon/short text version:
      Anterior alerts can be of either one or two configurations:
        Triangle/Triangle ("Δ XXX/Δ XXX"), in the case that an SP and a PSO alert we both activated.
        Triangle ("Δ XXX"), in the case that one or the other was activated
      Posterior alerts system can only be of the Triangle ("Δ XXX") configuration, and can be of the type ALL.
    The long text system can comprise the string: [STRING1] & "." & [STRING2].
      STRING1: Defined by User Config, as the combination of the [DESC COLOR] & [DESC PSO, SP, ALL]. For example "Likely Smith-Peterson osteotomy" or "Potential ALL release procedure"
      STRING2: Threshold text: Defined by User Config. For example: Yellow/PSO: "Target PDH<100% minimum PDH across all images". Red/SP: Target ADH>150% maximum ADH across all images"
  Sagittal Alignment alerts (SA).
    The icon/short text version of the Sagittal Alignment alerts is "Δ SA".
    The long text can be structured differently depending on whether the user configuration specified the "Rothenfluh" or the "Roussouly" method for determining Sagittal Alignment corrections.
      For users configured to "Rothenfluh": Long Text: system can comprise two strings, joined together: [STRING1] & "." & [STRING2].
        STRING1: "Potential Sagittal Alignment issues:"
        STRING2: Select which applies: "PI-LL is between X and Y" [this potentially applies to the yellow condition], "PI-LL is above Y." [this potentially applies to the red condition]. NOTE: X and Y are the User Config threshold values.
      For users configured to "Roussouly", there system can comprise two strings, joined together: [STRING1] & "." & [STRING2].
        STRING1: "Potential Sagittal Alignment issues:"
        STRING2: Include all that apply: "Type X Lordosis.", "Pelvic Tilt between X and Y" [this potentially applies to the yellow condition], "Pelvic Tilt is above Y." [this potentially applies to the red condition]. NOTE: X and Y are the User Config threshold values.
There can be the following alerting functionality on the following objects:
  Left Pane: Sagittal Alignment Diagram.
    For either Rothenfluh or Roussouly type Sagittal Alignment alerts, the alert icons Plus the short text can be visible when activated (see details in the Sagittal Alignment Diagram section for more info on placement).
    When one of the alert icons and short text is visible, when the user moves the mouse over the icon/text, a text box pops up with the Long Text for the alert.
  Left Pane: Disc Space View Diagram:
    The following alert items can be visible when activated:
      For the Rothenfluh type Sagittal Alignment alerts, the alert icon Plus the short text can be visible when activated (this appears on the rightmost column of the Dimensions Table).
      For Surgical consideration alerts, the alert icons plus short text can be visible when activated (this appears on the Distance From/To Diagram). See Disc Space View Diagram section for more details on placement.
    When one of the alert icons and short text is visible, when the user moves the mouse over the icon/text, a text box pops up with the Long Text for the alert.
  Right Pane: Surgery Summary:
    The following alert items can be visible when activated:
      For Rothenfluh & Roussouly type Sagittal Alignment alerts, the alert icon Plus the short text can be visible when activated (this appears in the middle section, see Surgery Summary section for more details on placement)
      For Surgical consideration alerts, the alert icons plus short text can be visible when activated (this appears column next to the column of checkboxes with the column header label "Fusion at this level?")
    When one of the alert icons and short text is visible, when the user moves the mouse over the icon/text, a text box pops up with the Long Text for the alert.
  Right Pane: Level Summary. Surgical Considerations
    In the upper sub panel for Surgical Considerations, each alert icon, short text, and long text are presented (Up to three sets possible, no mouse-over popups, format "Δ XXX: [LONG IEXT STRING]". Note that the icon/short text is different here than described above for the anterior alerts. In that section, a single combined icon/short text is created in the case that both SP and PSO alert is triggered. In this section, each gets its own row, and there is no single combined icon displayed in the case that both SP and PSO alerts are triggered).

Calculation Features:

There is a set of sequential calculations steps which provide updates to the Sagittal Alignment Diagram, Disc Space Diagram, Surgery Summary Object, Level Summary Object,:
  can be triggered by a range of actions, each action triggering a the calculations to start at a potentially different point in the calculation sequence:
    Actions that lead to the need to do the first, second, and third steps:
      Main Page: Surgery Summary object—Direct editing the [Additional Lordosis for Sagittal Alignment Corrections], [Upper Arc Additional Lordosis], [Lower Arc Additional Lordosis), changing the level excluded from lordosis calculations
      Main Page: Level Summary object—Directly editing [Total Segmental Lordosis], [Additional Segmental Lordosis for Sagittal Alignment Correction], [Segmental Correction for Anticipated Subsidence], or [Maximum Anticipated Anterior Subsidence]
      Main Page: Disc Space Diagram—Grab/rotate target construct line.
      Edit Lordosis (A3) modal window—Changing the levels excluded from lordosis calculations
      Lordosis Distribution Calculations modal windows—Editing [Additional Segmental Lordosis for Sagittal Alignment Corrections] (there may be up to five values, and the calculation is triggered by changes to any one of the up to five values), [Additional Lordosis for Sagittal Alignment Corrections], [Upper Arc Additional Lordosis], [Lower Arc Additional Lordosis],
      Edit Correction for Anticipated Subsidence modal window: Directly editing [Assumed Implant Length], [Segmental Correction for Anticipated Subsidence], or [Maximum Anticipated Anterior Subsidence]
    Actions that lead to a recalculation of the second and third steps include:
      Main Page: Surgery Summary object—changing the levels excluded from either disc height and offset calculations.
      Main Page: Disc Space Diagram—Grab/Drag of the Target Construct line
      Edit Midline Disc Height (A1 modal window: editing the Average Disc Height. (there may be up to five values, and the calc is triggered by changes to any one of the up to five values)
      Edit Offset (A2) modal window: editing the Average offset. (there may be up to five values, and the calculation is triggered by changes to any one of the up to five values)
    Actions that lead to the recalculation of the third step:
      Main Page: Surgery Summary object—changing the Lordosis Data source at a level.
First Step: Calculate Segmental Lordosis At each Level selected for fusion.

The sum equation for this calculation is
[Total Segmental Lordosis]=[Target Segmental Lordosis]+[Additional Segmental Lordosis for Sagittal Alignment Correction]+[Segmental Correction for Anticipated Subsidence].

This calculation can be performed upon any of the four user actions
  User directly inputs [Total Segmental Lordosis]
    This can be done via grab/rotate of the Disc Space Diagram, or by Direct Editing on the Level Summary Object.
    As the [Total Segmental Lordosis] value is changed by the user, the [Additional Segmental Lordosis for Sagittal Alignment Correction] is changed to keep the sum equation in balance.
  User changes [Target Segmental Lordosis]:
    This can be done via changing the set of levels excluded from lordosis calculations via interacting with the "exclude" checkboxes on the Surgery Summary page or the Edit Lordosis window
    As this value is changed, the [Total Segmental Lordosis] is changed to keep the sum equation in balance.
  User changes the [Additional Segmental Lordosis for Sagittal Alignment Correction]
    This can be done via:
    Directly editing the [Additional Segmental Lordosis for Sagittal Alignment Correction] on the Level Summary Object and the Lordosis Distribution Calculations modal windows
    In the case of
      ROTHENFLUH: Directly editing the [Additional Total Lordosis for Sagittal Alignment Correction] in the Surgery Summary Object and the Lordosis Distribution Calculations modal window.
      ROUSSOULY: Directly editing the either the [Upper Arc Additional Lordosis] or the [Lower Arc Additional Lordosis] for Sagittal Alignment Correction in the Surgery Summary Object and the Lordosis Distribution Calculations modal window.
    In either case, as this revised number is distributed across levels, the [Additional Segmental Lordosis for Sagittal Alignment Correction] system can change.
    Selecting or deselecting additional levels for fusion, on the row of checkboxes on the tabs on the upper part of the left pane, or on the column of checkboxes on the Surgery Summary Object
    As the [Additional Segmental Lordosis for Sagittal Alignment Correction] value is changed by the user, the [Total Segmental Lordosis] is changed to keep the sum equation in balance.
  User changes the [Segmental Correction for Anticipated Subsidence]
    This can be done via:
    direct edits to the [Segmental Correction for Anticipated Subsidence] via in the Level Summary Object and the Edit Correction for Anticipated Subsidence modal window
    Whenever [Segmental Correction for Anticipated Subsidence] changes, the value for [Maximum Anticipated Anterior Subsidence] changes as well, and the value for [Assumed Implant Length] is held constant.

Direct edits to the [Maximum Anticipated Anterior Subsidence] number via in the Level Summary Object and the Edit Correction for Anticipated Subsidence modal window Direct edits to the [Assumed Implant Length] number via in the Edit Correction for Anticipated Subsidence modal window

[Segmental Correction for Anticipated Subsidence], θ, system can change whenever the Maximum Anticipated Anterior Subsidence number (D) or the Assumed Implant Length number (B) changes: θ=ArcTangent [(A/2+B/2−C)/D]. Note: A=Length of superior edge of inferior vertebral body (from vertebral motion analysis). C=Offset (from vertebral motion analysis).

As the [Segmental Correction for Anticipated Subsidence] value is changed by the user, the [Total Segmental Lordosis] is changed to keep the sum equation in balance.

As will be appreciated by those skilled in the art, that there is one mechanism by which the for [Segmental Correction for Anticipated Subsidence] is automatically or semi-automatically updated by the system, via an automated or semi-automated adjustment to the [Maximum Anticipated Anterior Subsidence] number, which also trigger a recalculation according to this first step. See the description of the automatic adjustment later in this Calculation Features section, in the section titled "Computed values for [Segmental Correction for Anticipated Subsidence]"

Second Step: Calculate Geometric Transform at each level selected for fusion to Update the Disc Space Diagram and Distance From/To Diagrams
  The calculation is:
    The input for this calculation can be depth of
      the inferior vertebral body's superior endplate
      the superior vertebral body's inferior endplate
      Midline Disc Height
      Offset
      [Total Segmental Lordosis]
    This calculation can be performed according to the diagram of FIG. 12.
    The process steps of the Calculation can be:
      Origin is posterior superior corner of inferior vertebral body (point A).
      Horizontal origin is defined by point B, which gets placed along the horizontal origin at a distance from A equal to the depth of the inferior vertebral body's superior endplate.
      Point C is placed on the midpoint between A and B, moved upward to the midline disc height (avg. of PDH and AHD)
      Place a line going through C that is parallel to the [Total Segmental Lordosis].
      Place a point D along that line, such that the distance between A and D along the AB line is equal to the offset
      Place point E along that line at a distance from D equal to the depth of the superior vertebral body's inferior endplate
    The Output of this geometric transform is
      Coordinates of A, D, E, and B. A=0,0
      ADH: Length of the line dropped from D to the intersection of AB.
      PDH: Length of line dropped from E to the intersection of AB.
    The calculation is triggered by any of the following 3 actions:
      Performance of the First Step above.
      User Changes the Average Midline Disc Height, either by excluding level via interacting with the "exclude" checkboxes on the Surgery Summary page or the Edit Midline Disc Height modal window.
      Changing the Average Offset, either by excluding level via interacting with the "exclude" checkboxes on the Surgery Summary page or the Edit Offset modal window.

Third Step: Calculate Geometric Transform across all levels to update the Sagittal Alignment Diagram
  The calculation is:
    Stack Levels on top of levels, using the appropriate geometric points based on the current value of the Lordosis Data Source (from the Surgery Summary Object), to produce a new set of coordinates for the vertebral bodies and labels in the Sagittal Alignment Diagram.
    Calculate: Lumbar Lordosis (LL), PI-LL, [Additional Lordosis for Sagittal Alignment Corrections] default value, Lumbar Apex, Roussouly Type. (Note: PT, SS, and PI typically does not change).
  The calculation is triggered by any of the following 2 actions:
    Performance of the Second Step above
    Change to Lordosis Data Source on the Surgery Summary Object There are several calculation steps described, whose features are further defined:
  Computed values for Target Lordosis at a Level (for Rothenfluh and Roussouly) can be calculated according to the design of the Edit Lordosis (A3) modal window.
  Computed values for Additional Lordosis for Sagittal Alignment (Correction Rothenfluh), can be:
    For the total (across all levels selected for fusion), the computed value can be:
      for any patient wherein the PI-LL is above the user defined threshold, the value can be [PI-LL] Minus the target.
      For patients with PI-LL below the user defined threshold, the value can be zero (no null).
      The default value of the edit box for this value on the Surgery Summary Object system can assume either: (1) the computed value above, if the user config specifies that the default IS to include Sagittal Alignment corrections, or (2) zero if the user config specifies that the default is to NOT include sagittal alignment corrections.
    For segmental Additional Lordosis for Sagittal Alignment Correction, can be calculated according to the design of the Lordosis Distribution Calculations, Rothenfluh (B1) modal window.
  Computed values for Additional Lordosis for Sagittal Alignment (Roussouly), system can:
    Default for the Upper Arc and Lower Arc Additional Lordosis for Sagittal Alignment Correction is zero For segmental Additional Lordosis for Sagittal Alignment Correction, can be calculated according to the design of the Lordosis Distribution Calculations, Roussouly (B2) modal window.

Computed values for [Segmental Correction for Anticipated Subsidence]:

Can be calculated according to the design of the Edit Correction for Anticipated Subsidence (C1) modal window.

The [Maximum Anticipated Anterior Subsidence] value can be adjusted automatically or semi-automatically by the software based on the difference between the plumb line angle and the average angle (relative to the plumb line) between the superior edge of the inferior vertebral body and the inferior edge of the superior vertebral body. Whenever this difference is less than the value specified in user config, the [Maximum Anticipated Anterior Subsidence] value is adjusted by an amount as specified in user config, and then accordingly the [Segmental Correction for Anticipated Subsidence] is adjusted as well.

Lumbar Apex: This value can be calculated according to the following formula pseudo-code:

---

If MIN ( Abs ($PEA_{L3}$), Abs ($PEA_{L4}$), Abs ($PEA_{L5}$) ) = Abs ($PEA_{L3}$)
THEN LA =
    L3
    ELSE If Abs ($PEA_{L4}$) < Abs ($PEA_{L5}$), THEN LA = L4
    ELSE LA = L5
SS = Sacral Slope
LA = Lumbar Apex
$PEA_{LX}$ = Posterior edge angle (vs. plumb) for vertebral body X

---

Roussouly Type: This value can be calculated according to the following formula pseudo-code:

Roussouly typing is done based on two parameters, which can agree to get a result:

---

If SS < 35 AND LA = L5: Type text = "Type 1"
If SS < 35 AND LA = L4: Type text = "Type 2"
If (SS ≥ 35 AND ≤ 45) AND LA = L4: Type text = "Type 3"
If SS > 45, AND LA = L3 or higher: Type text = "Type 4"
No result scenarios:
    If SS < 35 AND LA=L3: Type text = "ERROR: Type 1-2 based on Sacral
        Slope, but apex is not L4-L5"
    If (SS ≥ 35 AND ≤ 45) AND (LA = L5 OR L3): Type text = "ERROR:
        Type 3 based on Sacral Slope, but apex is at [L5/L3] not L4"
    If SS > 45 AND (LA = L4 or L5): Type text = "ERROR: Type 4 based on
        Sacral Slope, but apex is at [L4/L5] not L3"
SS = Sacral Slope
LA = Lumbar Apex

---

Input File Features

The filenames that the system uses as input can be of the filename type: "XX_MMDDYYYY", where XX=First initial and last initial, and MMDDYYYY is the patient's date of birth.

The following data can be available from the input fileset:
For Each study,
  Atypical anatomy (L6, S2, no L5, etc.)? Boolean TRUE/FALSE [NOTE: Currently, this is FALSE. In other configurations, a variable might be used, which results in a value other than FALSE].
  PI, LL, SS, PT: Four different numbers. Non-integer (double). Degree units.
  Patient identifier:
    Patient name: Two Strings (first, last). If there is a middle initial, it will be contained with the first name string. All strings are of unspecified length (i.e. length not controlled).
    Date of birth: String of "YYYYMMDD"
    Sex: String "M" or "F"
  Template confirmation occurred? Boolean TRUE/FALSE [NOTE: Currently, this will is FALSE. In other configurations, a variable might be used, which results in a value other than FALSE].
For Each level: From standing neutral, get:
  In both % VBD and mm:
    ADH, PDH, midline and Offset: Non-integer (double). For % VBD, 1%=1 (not 0.01).
    Two instances of each data point (one in % VBD, one in mm)
  lordosis and max lordosis: Non-integer (double). Degree units.
  Max/min mobility (ADH, PDH, Offset) at each level. This is a set of min and max values for each of ADH, PDH, and Offset. Non-integer (double). Millimeter units. In the case of ADH and PDH, this is the millimeters to the min and max displacement relative to the anterior superior corner and posterior superior corner (respectively) of the inferior vertebral body of a level.
For Each vertebral body: From standing neutral, get:
  Angle measurements (vs. plumb): Angle of anterior edge, posterior edge, superior endplate and posterior endplates. Non-integer (double). Degree units.
  Coordinates for each of the four corners of each vertebral body. Non-integer (double) pair of (x,y) coordinates, where (1,1) is the upper left most point. Units will be in pixels or millimeters. Ideally the system should be able to handle both. These coordinates are used in the Sagittal balance diagram.
  Length of each of the four edges. Non-integer (double). Millimeter units.
  Labels of each vertebral body, and the location of where the labels system can go
Pdfs of report package (without images)
Image arrays. These are further specified below. The image arrays contain the following data elements:
  A set of 29 to 153 jpeg image files (without templates)
  Two arrays of pointers to files contained in this image set:
    5×11 array for Specified Views
    5×8 array for Min/Max views
  A 5×18 array, each element containing:
    two sets of 4 (x,y) points (8 sets in total), one each for the superior and inferior vertebral body. Each of these 8 sets of (x,y) points will be from an origin at the upper left hand corner of the associated image (the upper left point is (1,1)). Units will be in pixels or millimeters. Ideally the system should be able to handle both.
    Labels of each vertebral body, and the location of where the labels should be placed on the image
Further specification of image arrays
  Specific views:
    This system can include up to all 11 views (standing uncontrolled flex/ext/neutral, standing controlled flex/ex/neutral, lying controlled flex/ex/neutral, supine, prone). If views are missing they can be absent from the image array.

Each view will have a pelvic view and an inferior view, and some might additionally have superior view Therefore this set of images is 22 min and 33 max.

A 5×11 array of pointers needs to be created that lists all 5 Levels (L1/L2 through L5/S1) and all 11 views, such that for each cell there is a pointer to the appropriate image file that contains that vertebral body Min/Max Views:

In preparing the data, for each of the 5 Levels (L1/L2 through L5/S1), the following specific images need to be pulled and saved to the data structure:

Min lordosis, max lordosis (min lordosis is the largest absolute inter-vertebral angle, and max lordosis is the minimum absolute inter-vertebral angle)

Min ADH, Offset, and PDH. Max ADH, Offset and PDH.

This is a total of: [5 levels]×[4 min+4 max=8]=40 views.

These views, plus any of the 11 that are not already included in the 40 views above, are saved to the data file. This means that a min of 29 (if all 11 are included in the 40) and a max of 51 (if none of the 11 are included in the 40) images will be transferred over.

If there are superior as well as pelvic and inferior views, these numbers range from (i.e. min is still 29, but max is actually 153)

A data structure needs to be created that is a 5×8 array of pointers to image file names. This contains the specific pointer to each of the min or max view for each level.

Vertebral body location data

A 5×19 array needs to be created to contain the location data for the four points of the two vertebral bodies 5=5 levels 19=all views (the 11 specified views+8 min/max views)

Each element in the 5×19 array will have 2 sets of four (x,y) coordinates (relative to the upper left corner of the image), one set for the superior vertebral body, and one for the inferior vertebral body.

Alterations to the System

There can be a new user type: system user

Associated with a prescriber or a site

Multiple system users possible for each prescriber or site

The system user logs in via the portal, selects patients, then get downloaded an encrypted zipped file containing a rendered packet of data. Once the download is complete, the system records that this has been downloaded. It can be re-downloaded as many times as the user would like.

The download packet itself is a data structure that gets used by another program—the system—that runs on an unconnected console computer. The detailed data structure specification is given below:

The system will NOT render data packets if any of the following conditions apply. The system will need to present an appropriate error message to the user letting them know why the data packet cannot be rendered, and what (if anything) can be done to remedy the situation:

Templates have NOT been confirmed. Please confirm templates

Patient has anomalous anatomy. This type of patient cannot be processed using system.

Incomplete data. The vertebral motion analysis study was incomplete, and would need to be reprocessed to include data that is currently missing to be able to render a system file. [NOTE: All of the data listed below can be present (i.e. no "n/r" is any cell). An exception is image data: If all other data is complete but some expected views are missing, then the data can be rendered.]

A grid calibration was not done in the vertebral motion analysis study, which may be used for processing using system. The vertebral motion analysis study can be re-run, reprocessed, and then a system file can be rendered.

A millimeter calibration marker was either not included, or was not usable. The vertebral motion analysis study needs to be re-run, reprocessed, and then a system file can be rendered.

In engaging the systems and methods according to aspects of the disclosed subject matter the user may engage in one or more use sessions. Each use session may include a training session and/or surgical session. Additional data relating to performance may be compared from one or more use sessions for application in other surgical procedures.

Figure 13A:
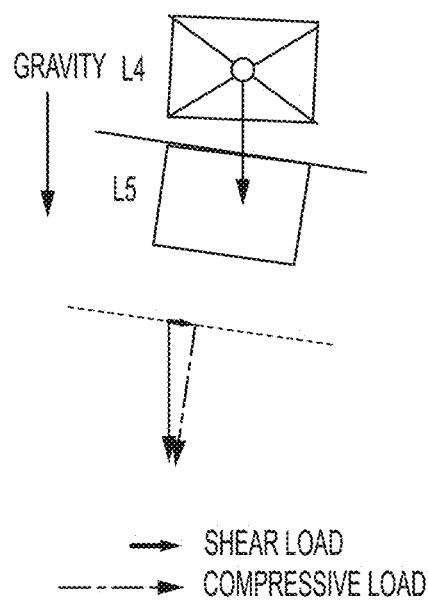
FIG. 13A-C illustrate methods for projecting loads.
Figure 13B:
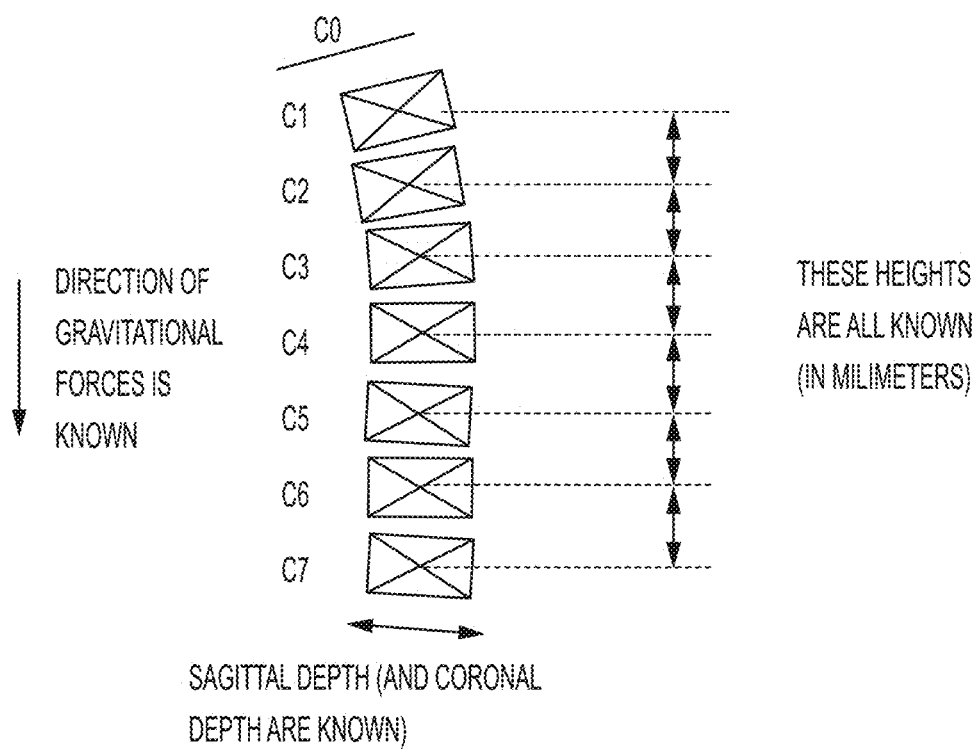
Figure 13C:
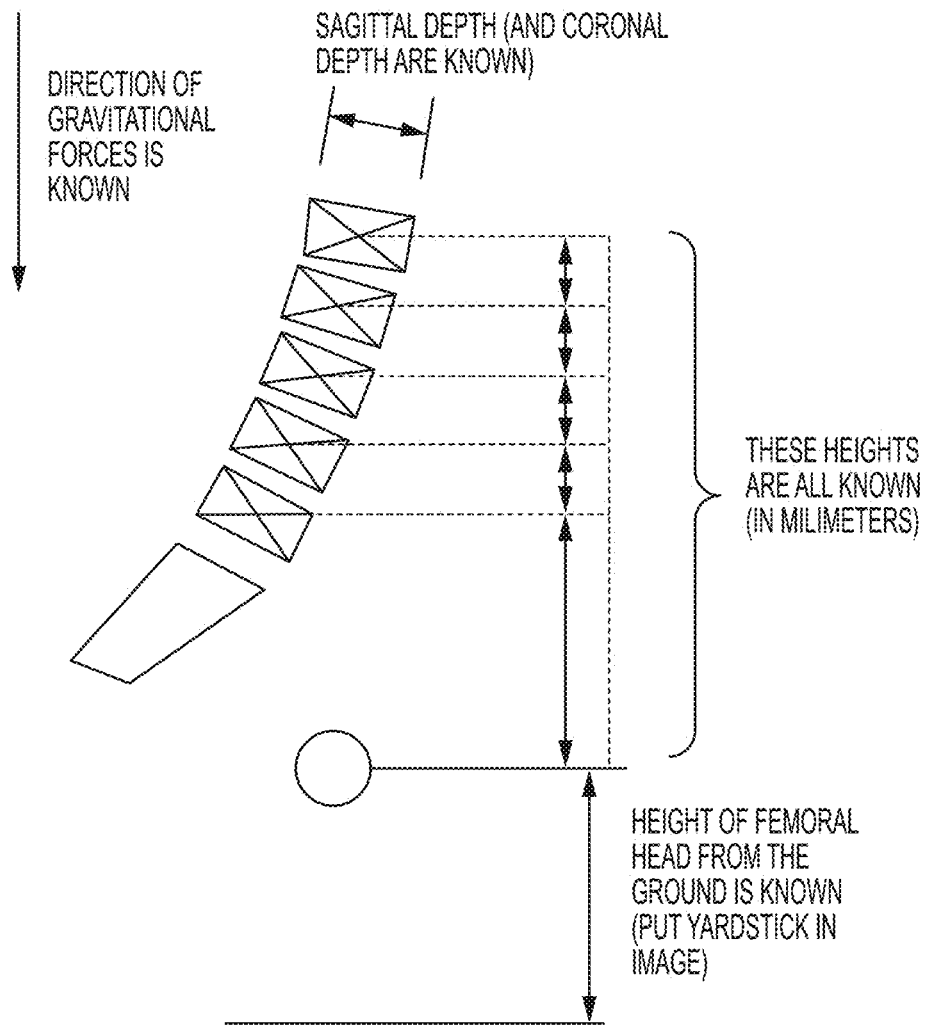

A fourth aspect of the disclosure is a method of modeling and projecting various loads across orthopedic implants prior to and during surgery. An input to this system is data regarding the position of patient spinal and other anatomy in various positions, including those that represent target physical conditions such as unassisted standing neutral postures. Knowing the spatial location of this anatomy, especially when these locations incorporate data that enables the anatomy to be placed in space relative to a gravitational plumb line, can be used to project forces at a specific level, and within a level at specific points. To acquire this data relative to a plumb line, a measurement system is used that incorporates an ability to image a plumb line, and that incorporates the ability to derive positional data for each vertebral body relative to this plumb line. See FIGS. 13A-C.

These forces can be projected using simple geometric relationships which account for normal gravitational loads that would occur, for example, during unassisted standing neutral postures. These forces could then be differentially projected post-operatively, assuming a specific type of geometry of the surgical construct, then substituting the pre-operative geometry with the assumed post-operative geometry at a surgical level, to project a new spatial relationship between spinal levels, and thus to project how forces may change as a consequence of the change in geometry at the operated level.

These forces can be projected in other ways that incorporates: (1) biomechanical modelling using standard biomechanical modelling software, (2) additional patient-specific parameters such as the cross sectional area of a muscle or muscle group in radiographic images, other imaging parameters, surface and/or needle electromyography and any associated measurements (such as applied force during surface electromyogram (EMG) data collection during isometric or isokinetic or some other form of functional testing).

These forces can be projected in a way that is relative, such that a single force measurement is given as a "high, medium, or low". These groupings may be defined by user settable thresholds. These forces will include sheer forces and compressive forces, at the anterior margin and the posterior margin of the implant (for a total of four force parameters. These force projections may incorporate specific information about the placement of a specific implant, such that intra-operatively implant placement can be input into the system to determine if any abnormally high forces are detected for a specific surgical construct.

These forces projections may incorporate target surgical construct geometry, as may be specified by a user in some way, to project how forces would change and what type of forces may result from a specific type of surgical construct.

The systems and methods according to aspects of the disclosed subject matter may utilize a variety of computer and computing systems, communications devices, networks and/or digital/logic devices for operation. Each may, in turn, be configurable to utilize a suitable computing device which can be manufactured with, loaded with and/or fetch from some storage device, and then execute, instructions that cause the computing device to perform a method according to aspects of the disclosed subject matter.

A computing device can include without limitation a desktop computing device, a networked computing device, a mobile user device such as a mobile phone, a smart phone and a cellular phone, a personal digital assistant ("PDA"), a tablet, a laptop and the like. In at least some configurations, a user can access and manipulate data via a browser application over a network, such as the Internet, to view and interact with digital content, such as screen displays. A display includes, for example, an interface that allows a visual presentation of data from a computing device. Access could be over or partially over other forms of computing and/or communications networks. A user may access a web-browser, e.g., to provide access to applications and data and other content located on a web-site or a web-page of a web-site.

A suitable computing device may include a processor to perform logic and other computing operations, e.g., a stand-alone computer processing unit ("CPU"), or hard wired logic as in a microcontroller, or a combination of both, and may execute instructions according to its operating system and the instructions to perform the steps of the method, or elements of the process. The user's computing device may be part of a network of computing devices and the methods of the disclosed subject matter may be performed by different computing devices associated with the network, perhaps in different physical locations, cooperating or otherwise interacting to perform a disclosed method. For example, a user's portable computing device may run an app alone or in conjunction with a remote computing device, such as a server on the Internet. For purposes of the present application, the term "computing device" includes any and all of the above discussed logic circuitry, communications devices and digital processing capabilities or combinations of these.

Certain embodiments of the disclosed subject matter may be described for illustrative purposes as steps of a method which may be executed on a computing device executing software, and illustrated, by way of example only, as a block diagram of a process flow. Such may also be considered as a software flow chart. Such block diagrams and like operational illustrations of a method performed or the operation of a computing device and any combination of blocks in a block diagram, can illustrate, as examples, software program code/instructions that can be provided to the computing device or at least abbreviated statements of the functionalities and operations performed by the computing device in executing the instructions. Some possible alternate implementation may involve the function, functionalities and operations noted in the blocks of a block diagram occurring out of the order noted in the block diagram, including occurring simultaneously or nearly so, or in another order or not occurring at all. Aspects of the disclosed subject matter may be implemented in parallel or seriatim in hardware, firmware, software or any combination(s) of these, co-located or remotely located, at least in part, from each other, e.g., in arrays or networks of computing devices, over interconnected networks, including the Internet, and the like.

The instructions may be stored on a suitable "machine readable medium" within a computing device or in communication with or otherwise accessible to the computing device. As used in the present application a machine readable medium is a tangible storage device and the instructions are stored in a non-transitory way. At the same time, during operation, the instructions may at some times be transitory, e.g., in transit from a remote storage device to a computing device over a communication link. However, when the machine readable medium is tangible and non-transitory, the instructions will be stored, for at least some period of time, in a memory storage device, such as a random access memory (RAM), read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or a remote server access over a network, or the like. When so stored, the software will constitute a "machine readable medium," that is both tangible and stores the instructions in a non-transitory form. At a minimum, therefore, the machine readable medium storing instructions for execution on an associated computing device will be "tangible" and "non-transitory" at the time of execution of instructions by a processor of a computing device and when the instructions are being stored for subsequent access by a computing device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A machine readable medium containing instructions stored on a non-transitory computer readable medium that, when executed by a computing device, cause the computing device to perform a method, the method comprising:

receiving an input dataset comprising one or more medical images containing a spine level of interest for a patient; and generating an optimized anatomical dataset for the spine level of interest wherein the optimized anatomical data set comprises one or more of a target disc height, a target anterior-posterior offset, and a target lordosis angle, and further wherein the step of generating an optimized anatomical dataset for the spine level of interest comprises the steps of:

identifying zero, one, or more visible spine levels in the one or more medical images to exclude from analysis; and accessing one or more image-derived measurements of a disc height measurement, an anterior-posterior offset measurement, and a sagittal lordosis angle measurement for one or more non-excluded spine levels; and applying a function to the one or more measurements from accessing one or more image-derived measurements to generate an optimized value for the spine level of interest for one or more of the target disc height, the target anterior-posterior offset, and the target lordosis angle.

2. The machine readable medium of claim 1, wherein the function receives an input and applies one or more adjustments to correct for an assumed post-operative subsidence of an interbody device over time.

3. The machine readable medium of claim 2, wherein the one or more adjustments is a disc height adjustment, an anterior-posterior offset adjustment, and a lordosis angle adjustment.

4. The machine readable medium of claim 1, wherein the one or more medical images excluded from analysis is excluded independently for one or more of an excluded disc height measurement, an excluded anterior-posterior offset, and an excluded sagittal lordosis angle.

5. The machine readable medium of claim 1, wherein the function is one of an average function and a distribution function, and further wherein an input is selected from a medical literature.

6. The machine readable medium of claim 1, wherein a surgical navigation system user may specify a gross lordosis target for an entire region of a spine and wherein the function distributes one or more gross lordosis regional targets across a user-specified set of levels targeted for fusion surgery.

7. A processor for generating estimates of a weight carried at a spine level of interest, wherein the processor is programmed to execute:

accessing an input dataset for a patient comprising a weight of the patient, one or more image-derived measurements of a spatial relationships between two or more vertebral bodies visible within one or more images;

allowing a user to specify a spine level of interest; and projecting an estimated weight carried at the spine level of interest by:

looking-up one or more values from a previously published mass distribution function, wherein the mass distribution function comprises a set of percentage values associated with various bodily regions such that the sum of the set of percentage values equals 100%;

summing x from the mass distribution function elements for all bodily regions cranial to a spinal region of interest;

calculating y from the image-derived measurements of the spatial relationships between vertebral bodies from the input dataset, by determining an estimated percentage of the region of interest that is cranial to a spinal level of interest;

summing x and y; and multiplying the sum of x and y by a weight of the patient to determine the weight carried at the spine level of interest.

8. The processor for generating estimates of the weight carried at the spine level of interest of claim 7 further comprising:

calculating a sheer and a compressive component of the weight carried at the spine level of interest, using the image-derived measurements of the angulation between vertebral body endplates and a plumb line.

9. The processor for generating estimates of the weight carried at the spine level of interest of claim 7 wherein the input dataset contains patient-specific data and wherein the computational routine incorporates a lookup function that returns a mass distribution which is a function of the patient-specific data.

10. The processor for generating estimates of the weight carried at the spine level of interest of claim 9 wherein the patient-specific data is selected from age, gender, and height.

11. The processor for generating estimates of the weight carried at the spine level of interest of claim 7 wherein previously published mass distribution function is one selected by the user from among a set of available functions.

12. A processor for use with surgical navigation systems used for spinal surgery wherein the processor is programmed to execute:

receiving an input dataset comprising one or more medical images containing a spine level of interest; and generating measurements of an operating range of the spine level of interest, comprising measurements of at least one of a minimum linear displacement between a pair of adjacent vertebral body corner-points from the spine level of interest and a maximum linear displacement between a pair of adjacent vertebral body corner-points from the spine level of interest by executing a computational process comprising:

accessing one or more medical images containing the spine level of interest from the input dataset, and further accessing one or more measurements from each image of at least one of the minimum linear displacement and the maximum linear displacement; and applying at least one of a maximum function and a minimum function to the measurement sets to determine a maximum linear displacement value for a pair of adjacent corner points and a minimum linear displacement values for the pair of adjacent corner-points; and rendering data usable by a surgical navigation system based on the operating range measurements.

13. The processor of claim 12, wherein the rendering of data usable by a surgical navigation system supports a visual display of the operating range measurements by the surgical navigation system.

14. The processor of claim 12, wherein the data rendered triggers an alert to a surgical navigation system user when the operating range measurement for the spine level of interest is outside of a user-determined threshold value.

* * * * *